United States Patent
Bayon

(10) Patent No.: US 11,058,332 B2
(45) Date of Patent: Jul. 13, 2021

(54) SYSTEM AND METHOD FOR EARLY DETECTION OF POST-SURGERY INFECTION

(71) Applicant: Sofradim Production, Trévoux (FR)

(72) Inventor: Yves Bayon, Rhone (FR)

(73) Assignee: Sofradim Production, Trévoux (FR)

( * ) Notice: Subject to any disclaimer, the term of this patent is extended or adjusted under 35 U.S.C. 154(b) by 494 days.

(21) Appl. No.: 15/512,251

(22) PCT Filed: Sep. 25, 2015

(86) PCT No.: PCT/IB2015/001971
§ 371 (c)(1),
(2) Date: Mar. 17, 2017

(87) PCT Pub. No.: WO2016/046634
PCT Pub. Date: Mar. 31, 2016

(65) Prior Publication Data
US 2017/0281064 A1   Oct. 5, 2017

(30) Foreign Application Priority Data

Sep. 26, 2014  (EP) ..................................... 14306496
Sep. 18, 2015  (EP) ..................................... 15306462

(51) Int. Cl.
*A61B 5/145*   (2006.01)
*A61B 5/00*   (2006.01)
*A61M 1/00*   (2006.01)

(52) U.S. Cl.
CPC ...... *A61B 5/14546* (2013.01); *A61B 5/14539* (2013.01); *A61B 5/412* (2013.01); *A61M 1/0025* (2014.02); *A61B 2562/0271* (2013.01)

(58) Field of Classification Search
CPC . A61B 5/145; A61B 5/14546; A61B 5/14539; A61B 5/412; A61B 5/41; A61B 2562/0271; A61M 1/0025
See application file for complete search history.

(56) References Cited

U.S. PATENT DOCUMENTS 7,692,219 B1 *   4/2010   Holm-Kennedy ..... B82Y 10/00
                                                            257/253
8,750,396 B2      6/2014   Carnes
                          (Continued)

FOREIGN PATENT DOCUMENTS

CN       102057275 A       5/2011
CN       103800994 A       5/2014
WO   WO 2014/043650 A2     3/2014

OTHER PUBLICATIONS

Australian Examination Report issued in Australian Application No. 2015323511 dated May 30, 2019, 3 pages.
(Continued)

*Primary Examiner* — Patrick Fernandes

(57) ABSTRACT

In-vivo systems and methods for the detection of early signs of post-surgery infection are described. The in-vivo systems include a drain system with a tube configured to drain fluids from a surgery site, at least one sensor unit for sensing the presence of at least one infection biomarker, a processor for processing a signal generated by the at least one sensor unit, a transmitter for transmitting the signal, and a notification system for receiving the signal, analyzing the signal by comparing it to a threshold, determining presence of infection, and generating an indication on the presence of infection.

15 Claims, 6 Drawing Sheets

(56) References Cited

U.S. PATENT DOCUMENTS

| | | | |
|---|---|---|---|
| 2006/0282028 A1* | 12/2006 | Howard | A61M 27/00 602/2 |
| 2007/0275423 A1* | 11/2007 | Sebastian | C12Q 1/04 435/7.71 |
| 2008/0064980 A1 | 3/2008 | Lee et al. | |
| 2008/0262322 A1 | 10/2008 | Gerber et al. | |
| 2008/0269582 A1* | 10/2008 | Mansour | A61B 5/14542 600/357 |
| 2009/0155770 A1 | 6/2009 | Brown et al. | |
| 2009/0171170 A1* | 7/2009 | Li | A61B 5/00 600/301 |
| 2009/0182210 A1* | 7/2009 | Taro | A61B 5/0836 600/323 |
| 2011/0060204 A1* | 3/2011 | Weston | A61M 1/0088 600/364 |
| 2015/0019257 A1 | 1/2015 | Doyle et al. | |

OTHER PUBLICATIONS

Chinese Office Action issued in Chinese Application No. 201580051994.2 dated May 15, 2019, 16 pages.

International Search Report for PCT/IB2015/001971 date of completion is Jan. 25, 2016 (4 pages).

Chalupa P et al, "Evaluation of potential biomarkers for the discrimination of bacterial and viral infections", Infection ; A Journal of Infectious Disease, Urban & Vogel, MU, (Jul. 1, 2011), vol. 39, No. 5, doi:10.1007/S15010-011-0126-4, ISSN 1439-0973, pp. 411-417, XP019966308 [A] 1-18 * the whole document *.

European Search Report for EP 15306462.1 date of completion is Feb. 1, 2016 (10 pages).

Chinese Office Action issued in corresponding Appl. No. CN201580051994.2 dated Dec. 6, 2019, together with English language translation (12 pages).

Chinese Office Action issued in Chinese Application No. 201580051994.2 dated Mar. 18, 2020, together with English language translation (12 pages).

Decision of Rejection issued in corresponding Appl. No. CN 201580051994.2 dated Jun. 22, 2020 (5 pages) together with English language translation (1 page).

Examination report No. 1 issued in corresponding Australian Appl. No. 2020200006 dated Sep. 8, 2020 (5 pages).

* cited by examiner

SYSTEM AND METHOD FOR EARLY DETECTION OF POST-SURGERY INFECTION

CROSS-REFERENCE TO RELATED APPLICATIONS

This application claims benefit of and priority to European Patent Application Serial No. PCT/IB2015/001971 filed Sep. 25, 2015, which claims benefit of and priority to European Patent Application Serial No. 15306462.1 filed Sep. 18, 2015, which claims benefit of and priority to European Patent Application Serial No. 14306496.2 filed Sep. 26, 2014, and the disclosures of each of the above-identified applications are hereby incorporated by reference in their entirety.

FIELD OF THE INVENTION

This application relates to the field of systems and methods of detection. In particular, the present invention relates to systems and methods for detection of early signs of post-surgery infection.

BACKGROUND

In some cases, a patient that undergoes surgery may require a drain left in the surgery site for about 1-2 days (or sometimes for even longer periods of time, e.g., 1-2 weeks). Typically, such drains are monitored by the medical staff every few hours, in order to determine the state of the surgery site, e.g., whether the surgery site is healing properly with no interruptions or whether an infection may have developed. When monitoring of such drains takes place only every few hours, an infection may already be at a progressive stage before it is noticed and properly treated. Furthermore, the signs that physicians usually examine in order to detect presence of infection are signs that appear when an infection is in progressive state, and which may not be detectable by typical monitoring at an early stage of the infection. There is, therefore, a need for improved systems and methods for early and continuous detection of post-surgery infection.

SUMMARY OF THE INVENTION

Embodiments of the present invention provide in-vivo systems and methods for early and continuous detection of infection. These systems may include external tubes with capabilities of monitoring in-vivo fluids flowing there through. Examples for such systems may include urinary catheters, peritoneal dialysis systems, hemo/renal dialysis systems, shunts, catheters, or drain systems located in close proximity to a surgical site, for monitoring post-surgery infection. Such systems enable detection of early signs of infection, when an infection is in its initial stage only, well before it becomes progressive and severe, and thus appropriate treatment may be provided well before the patient's or surgery site's condition is critical. These systems may also incorporate real-time continuous automatic self-monitoring without human intervention, and may generate an indication of the presence and even the various stages of infection, if any, e.g., mild, progressive or severe. Either the care provider or the patient may be notified by the indication as to presence (and possibly the stage) of infection. In some embodiments, systems of the invention include sensors for sensing presence of various infection biomarkers, i.e., biomarkers that indicate presence of infection. Such infection biomarkers may, in some cases, be direct biomarkers, which may increase when an infection occurs. Direct infection biomarkers may be bacteria species. For example, direct infection biomarkers may be bacteria commonly associated with clinical/nosocomial infections including *Staphylococcus, Escherichia, Pseudomonas, Streptococcus, Enterococcus* and *Enterobacter* species, bacteria associated with gastro-intestinal leaks such as commensal bacteria commonly found in the gastro-intestinal bacteria flora and/or alternatively pathogen bacteria potentially colonizing the gastro-intestinal tract. In addition, direct infection biomarkers may also include non specific bacteria species, which produce and release, for example, sulfur related gases, hydrogen, and ammonia. Direct biomarkers of specific bacteria may further include bacteria which release or "exhale" volatile organic compounds, by endogenous metabolism of these bacteria. That is, following an addition of defined chemicals or biochemicals to the bacteria's environment, the chemicals/biochemicals are metabolized or transformed into volatile organic compounds by these bacteria species.

In some embodiments, direct infection biomarkers may include specific genetic material signatures, e.g., bacteria species or subspecies specific DNA primers, which may be used for at least the semi-quantification (in Colony Forming Units (CFU) per milliliter, i.e., [CFU/ml]) of bacteria of interest by polymerase chain reaction (PCR).

However, in other cases, infection biomarkers may be indirect biomarkers that are an indirect byproduct of presence of infection, e.g., pH, lactic acid, exudate flow, fluid viscosity, local/systemic oxygen saturation, and local/systemic temperature. Further examples of indirect biomarkers may be immune-modulating mediators, such as IL-1, IL-6, IL-10 and TNF-α, pancreas enzymes such as amylase, inflammatory parameters such as Lipopolysaccharide Binding Protein (LBP), and metabolic parameters such as glucose.

Changes (e.g., increase or decrease) in the level or concentration of indirect biomarkers may indicate on the presence of infection.

In some embodiments, the systems include more than one sensor for sensing more than one type of infection biomarker, either direct or indirect. In some embodiments, there may be a combination of sensors, some for sensing indirect infection biomarkers and some for sensing direct infection biomarkers.

According to some embodiments, a system for detecting early signs of post-surgery infection in a patient may include a drain system comprising a tube configured to drain fluids from a surgery site, at least one sensor unit for sensing the presence of at least one infection biomarker, a processor for processing a signal generated by the at least one sensor unit, a transmitter for transmitting the processed signal, and a notification system for receiving the processed signal, analyzing the processed signal by comparing it to a threshold (either a predetermined threshold or an adaptive and changing threshold that may be based on changing parameters of the sensed biomarkers and/or on the rate of change of such parameters), determining presence of infection, and generating an indication on the presence of infection.

In some embodiments, the drain system may further comprise a container into which the fluids passing through the tube are drained.

In some embodiments, the at least one infection biomarker is selected from a group of indirect infection biomarkers consisting of: pH, lactic acid, and flow rate of exudate, or a combination thereof. Further examples of indirect biomarkers, which an infection biomarker may be selected from may be immune-modulating mediators, such as IL-1, IL-6, IL-10 and TNF-.alpha., pancreas enzymes such as amylase, inflammatory parameters such as Lipopolysaccharide Binding Protein (LBP), and metabolic parameters such as glucose. In other embodiments, the at least one infection biomarker is a direct infection biomarker, which is a bacteria specie selected from the group consisting of: *Escherichia coli, Pseudomonas* spp., *Pseudomonas aeruginosa, Pseudomonas putida, Staphylococcus* spp., *Staphylococcus aureus, Staphylococcus epidermidis, Streptococcus* spp., *Enterococcus* spp., *Klebsiella* spp., *Proteus* spp., *Serratia* spp., *Morganella* spp. and other Enterobacteriaceae, or a combination thereof. In other embodiments, other bacteria specie may be selected. In some embodiments, the direct infection biomarker may include specific genetic material signatures, e.g., bacteria species or subspecies specific DNA primers, which may be used for at least the semi-quantification (in Colony Forming Units (CFU) per milliliter, i.e., [CFU/ml]) of bacteria of interest by polymerase chain reaction (PCR).

According to some embodiments, the system may comprise a first sensor for sensing an indirect infection biomarker selected from the group consisting of: pH, lactic acid, and flow rate of exudate, or a combination thereof, and a second sensor for sensing a direct infection biomarker selected from the group consisting of: *Escherichia coli, Pseudomonas* spp., *Pseudomonas aeruginosa, Pseudomonas putida, Staphylococcus* spp., *Staphylococcus aureus, Staphylococcus epidermidis, Streptococcus* spp., *Enterococcus* spp., *Klebsiella* spp., *Proteus* spp., *Serratia* spp., *Morganella* spp. and other Enterobacteriaceae, or a combination thereof. In such embodiments, the notification system comprises an analyzer for analyzing signals detected by the first and second sensors, and determining the presence of infection.

According to some embodiments, the notification system comprises an analyzer for analyzing the processed signal and determining the presence of infection. In some embodiments, the analyzer further determines the stage of infection.

In some embodiments, when said infection biomarker is pH; a first indication may be generated if the level of pH is equal to or below 7.1, and a second indication may be generated if the level of pH is equal to or below 6.8. When said infection biomarker is lactic acid; a first indication may be generated during the first hour post-surgery if the concentration of lactic acid is equal to or above a threshold of 3 mM, a second indication may be generated if the concentration of lactic acid is above the threshold for 6 hours after the first indication, and a third indication may be generated if the concentration of lactic acid is above the threshold for 24 hours after the first indication.

In some embodiments, when said infection biomarkers are immune-modulating mediators, such as IL-1, IL-6, IL-10 and TNFα; a first indication may be generated if the level of at least one of these mediators is above 100% of a baseline/threshold value. In some embodiments, the baseline value may be obtained during the surgery or from the very first fractions of the collected exudates. A second indication may be generated if the level of at least one of these mediators is above 200% of the baseline value, or if the level of at least two of these mediators is above 100% of the baseline value, or if such levels are observed with an increasing trend over at least two consecutive measurements within intervals in the range of 4 to 24 hours.

In some embodiments, when said infection biomarker is LBP; a first indication may be generated if the level of LBP is above 100% of a baseline value. In some embodiments, the baseline value may be obtained during the surgery or from the very first fractions of the collected exudates. A second indication may be generated if the level of LBP is above 200% of the baseline value, or if the level of LBP is observed with an increasing trend over at least two consecutive measurements within intervals in the range of 4 to 24 hours. When said biomarker is glucose; a first indication may be generated if the level of glucose is below at least 20% of a normal value (indicatively 8 [mmol/l]), and with a decreasing trend during at least a day, while a second indication may be generated if the level of glucose is below 30% of the baseline/normal value with a decreasing trend during at least 2 days. When said biomarker is amylase; a first indication may be generated if the level of amylase is above 100 U/l, before the first 24 hours post-surgery, while a second indication may be generated if such level of amylase of above 100 U/l is observed over at least two consecutive measurements within intervals in the range of 4 to 24 hours.

In some embodiments, when the infection biomarker is a flow rate of exudate; a first indication may be generated 6 hours post-surgery if the flow rate is above 5 [ml/hr], a second indication may be generated 6 hours post-surgery if the flow rate is above 10 [ml/hr], and a third indication may be generated 6 hours post-surgery if the flow rate is above 20 [ml/hr]. When the infection biomarker is a non-hemolytic bacteria specie; a first indication may be generated if Colony Forming Units (CFU) is above $10^2$ [CFU/ml], a second indication may be generated if CFU is above $10^3$ [CFU/ml], and a third indication may be generated if CFU is above $10^4$ [CFU/ml]. When the infection biomarker is a hemolytic bacteria specie (e.g., *S aureus*, hemolytic Streptococci, hemolytic *E. coli* subspecies); a first indication may be generated if Colony Forming Units (CFU) is above $10^1$ [CFU/ml], a second indication may be generated if CFU is above $10^2$ [CFU/ml], and a third indication may be generated if CFU is above $10^3$ [CFU/ml].

In some embodiments, the threshold may be predetermined based on, for example experiments, whereas in other embodiments, the threshold may be adjustable and may be changed by the notification system according to changes in the trend of the parameters of the at least one infection biomarker that are sensed by the at least one sensor.

According to some embodiments, the transmitter wirelessly transmits the processed signals to the notification system. In some embodiments, an indication may be displayed on a display unit, e.g., a screen.

In some embodiments, the sensor may sense the presence of infection biomarkers continuously. In other embodiments, the sensor may sense the presence of infection biomarkers periodically, e.g., every few minutes or even within periods of time shorter than 1 minute. Typically, the periods during which the sensors may sense presence of the infection biomarkers may be designed to correspond to the type of biomarker.

In some embodiments, typically when the infection biomarker is an indirect biomarker, the sensor may be located along the tube. Yet, in other embodiments, typically when the infection biomarker is a direct biomarker, the sensor may be located within the container. In yet other embodiments, when infection biomarkers are indirect biomarkers such as immune-modulating mediators (e.g., IL-1, IL-6, IL-10 and TNFα) or LBP, or when infection biomarkers are direct biomarkers such as bacteria DNA, which are specifically detected and identified by PCR DNA primers; theses biomarkers cannot be sensed continuously along the tube.

Therefore, in such cases, the tube may be equipped with a system that enables collection of samples, preferably semi-automatically, more preferably automatically, for detection and measurements of the markers of interest by point of care (POC) analyzers.

According to some embodiments, a method for determining early signs of post-surgery infection in a patient may comprise the steps of: sensing presence of at least one infection biomarker by using a sensor incorporated in a drain system, processing signals generated by the sensor, transmitting the processed signals to a notification system, receiving the processed signals by the notification system, analyzing the processed signals by comparing the signals to a threshold, and determining the presence of infection.

According to some embodiments, when infection biomarkers cannot be sensed continuously along the tube, a method for determining early signs of post-surgery infection in a patient may comprise the steps of: measuring presence of at least one infection biomarker by using a point of care (POC) analyzer for examining samples collected in a drain system, processing signals generated by the POC analyzer, transmitting the processed signals to a notification system, receiving the processed signals by the notification system, analyzing the processed signals by comparing the signals to a threshold, and determining the presence of infection.

In some embodiments, the method may further comprise the step of generating an indication on presence of infection, based on signals generated either by one or more sensors incorporated in the drain system, or by POC analyzers, or by any combination of the above sensors or analyzers. In some embodiments, the step of sensing presence of infection biomarkers may be carried out continuously, while in other embodiments, the step of sensing presence of infection biomarkers may be carried out periodically.

BRIEF DESCRIPTION OF THE INVENTION

The present invention will be understood and appreciated more fully from the following detailed description taken in conjunction with the appended drawings in which.

Figure 1:
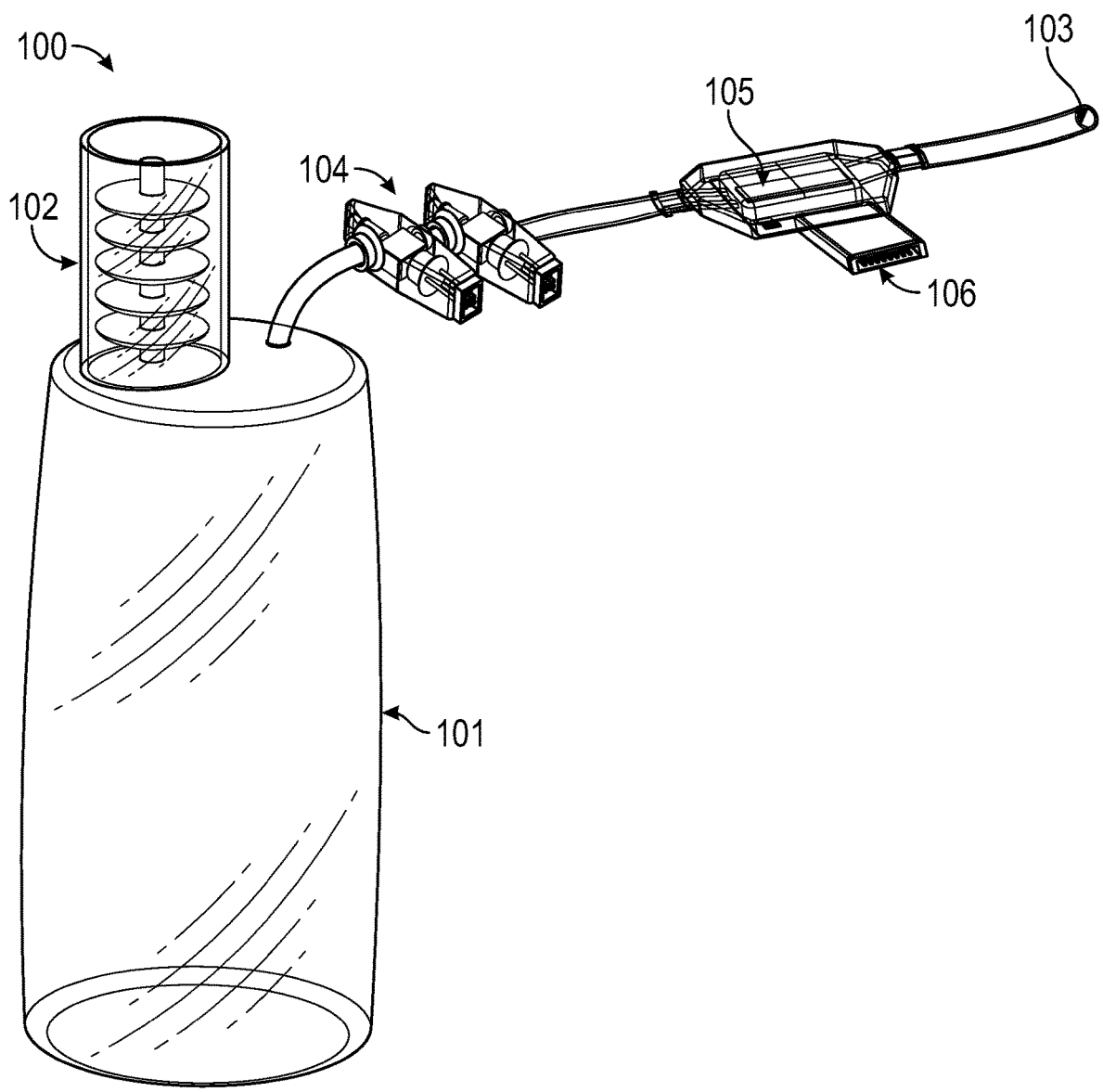
FIG. 1 is a schematic illustration of a drain system for detection of post-surgery infection, in accordance with an embodiment of the invention.

It will be appreciated that, for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as to not obscure the present invention.

Reference is now made to FIG. 1, which is a schematic illustration of a drain system for detection of post-surgery infection, in accordance with an embodiment of the invention. Drain system 100 may comprise a drain tube 103, which is configured to drain in-vivo fluids that are accumulating in close proximity to the surgery site. Tube 103 may connect between the surgery site and a container or canister 101. The in-vivo fluids that pass through tube 103 may gather in container 101, such that drained fluids are collected within container 101. Drain systems of such type, which comprise a tube and container into which fluids drain, are known as closed drain systems. In other embodiments, drain system 100 may be an open drain system, while not comprising a container, and thus fluids are drained onto a dressing or something of the sort. However, closed drain systems provide airtight circuits that prevent various contaminations from entering the surgery site, in a more efficient manner compared to open drain systems, thus system 100 may preferably be a closed drain system.

In some embodiments, drain system 100 may comprise a suction element 102, which may cause low or high pressure in order to actively suck fluids from the surgery site through tube 103 and into container 101. However, in other embodiments, drain system 100 need not comprise an active suction element 102, and drainage from the surgery site may operate passively.

In some embodiments, drain system 100 may further comprise various types of sensors for sensing presence of either direct infection biomarkers, e.g., by sensor system 104, or indirect infection biomarkers, e.g., by sensor system 105. Direct infection biomarkers may be various types of bacteria or bacteria byproducts that may be present within in-vivo fluids flowing from the surgery site, at very early stages of an infection that may begin at the surgery site following surgery. When infection occurs at the surgery site, the concentration of such direct infection biomarkers may increase, thus monitoring presence and concentration of direct infection biomarkers, may indicate on presence of infection, and even on the stage of infection, whether, for example, mild, progressive or severe. Direct infection biomarkers may, for example, be bacteria commonly associated with clinical/nosocomial infections including *Staphylococcus, Escherichia, Pseudomonas, Streptococcus, Enterococcus, Serratia, Klebsiella, Morganella, Proteus* and other *Enterobacter* species, bacteria associated with gastro-intestinal leaks such as commensal bacteria commonly found in the gastro-intestinal bacteria flora and/or alternatively pathogen bacteria potentially colonizing the gastro-intestinal tract. In addition, direct infection biomarkers may also include nonspecific bacteria species, which produce and release, for example, sulfur related gases, hydrogen, and ammonia. Direct biomarkers of specific bacteria may further include bacteria which release or "exhale" volatile organic compounds, by the metabolism of these bacteria. That is, following an addition of defined chemicals or biochemicals to the bacteria's environment, the chemicals/biochemicals are metabolized (either by endogenous metabolism or by exogenous metabolism of these bacteria) or transformed into volatile organic compounds by these bacteria species. In some embodiments, direct infection biomarkers may include specific genetic material signatures, e.g., bacteria species or subspecies specific DNA primers, which may be used for at least the semi-quantification (in Colony Forming Units (CFU) per milliliter, i.e., [CFU/ml]) of bacteria of interest by polymerase chain reaction (PCR).

Indirect infection biomarkers may be biomarkers that are an indirect byproduct of presence of infection, e.g., pH, lactic acid, exudate flow, fluid viscosity, local/systemic oxygen saturation, and local/systemic temperature. For example, when an infection occurs in the surgery site, pH may decrease relatively to standard pH of in-vivo fluids. Thus, monitoring the level of pH may indicate on presence of infection. Furthermore, the level of pH, and/or the time it took the pH level to decrease to its new lower level may even indicate on the stage of infection, e.g., mild, progressive or severe. If the infection biomarker is chosen to be lactic acid, then in presence of infection, the concentration of lactic acid is expected to increase rapidly, thus a sensor should be able to detect lactic acid presence and concentration. Further examples of indirect biomarkers may be immune-modulating mediators, such as IL-1, IL-6, IL-10 and TNF-α, pancreas enzymes such as amylase, inflammatory parameters such as Lipopolysaccharide Binding Protein (LBP), and metabolic parameters such as glucose.

In some embodiments, system 100 may comprise more than one sensor for sensing more than one type of infection biomarker. In some embodiments, there may be a combination of sensors, some for sensing indirect infection biomarkers and some for sensing direct infection biomarkers. For example, system 100 may only comprise sensor system 104 for sensing direct infection biomarkers. System 100, and thereby sensor system 104 may comprise more than one sensor unit for sensing more than one type of direct infection biomarkers. In other embodiments, system 100 may only comprise sensor system 105 for sensing indirect infection biomarkers. System 100, and thereby sensor system 105 may comprise more than one type of sensor unit for sensing more than one type of indirect infection biomarkers. Yet, in other embodiments, system 100 may comprise a combination of sensor system 104 for sensing indirect infection biomarkers and sensor system 105 for sensing indirect infection biomarkers. System 100 may comprise more than one type of sensor units for sensing more than one type of direct infection biomarkers (e.g., sensor units that are incorporated in sensor system 104), as well as more than one type of sensor units for sensing more than one type of indirect infection biomarkers (e.g., sensor units that are incorporated in sensor system 105). Typically, the more types of biomarkers that system 100 is configured to detect, the more accurate system 100 may be with detecting presence of infection at the surgery site, and furthermore with detecting the stage of infection. Any combination of sensors and any number of sensors may be incorporated as part of system 100. For example, sensor system 104 may comprise a sensor for detecting *Staphylococcus*, and sensor system 105 may comprise one sensor unit for detecting pH levels and another sensor unit for detecting concentration of lactic acid. Other embodiments may comprise other combinations.

In some embodiments, each of sensor systems 104 and/or 105 may be connected to an electronic board 106. Electronic board 106 may comprise a transmitter and antenna (not shown) that may transfer detections of the biomarkers by sensor systems 104 and/or 105 to an external receiver (as illustrated in system 200, FIG. 4). Electronic board 106 may comprise a power supply, e.g., at least one battery for supplying power to all of the electronic components within. Electronic board 106 may further comprise a processor (not shown), for processing signals generated by at least one sensor systems 104 and/or 105 prior to the signals being transmitted to an external receiver. The processor within electronic board 106 may perform complete processing of the signals generated by the sensors, such that the transmitted signals may be displayed to a user or may be used to generate a notification to the user with respect to presence of infection, and in some cases with respect to the stage of infection. In other embodiments, the processor may only perform initial processing on the signals generated by the sensors, and then the processed signals may be transmitted to an external receiver for further processing.

Figure 2:
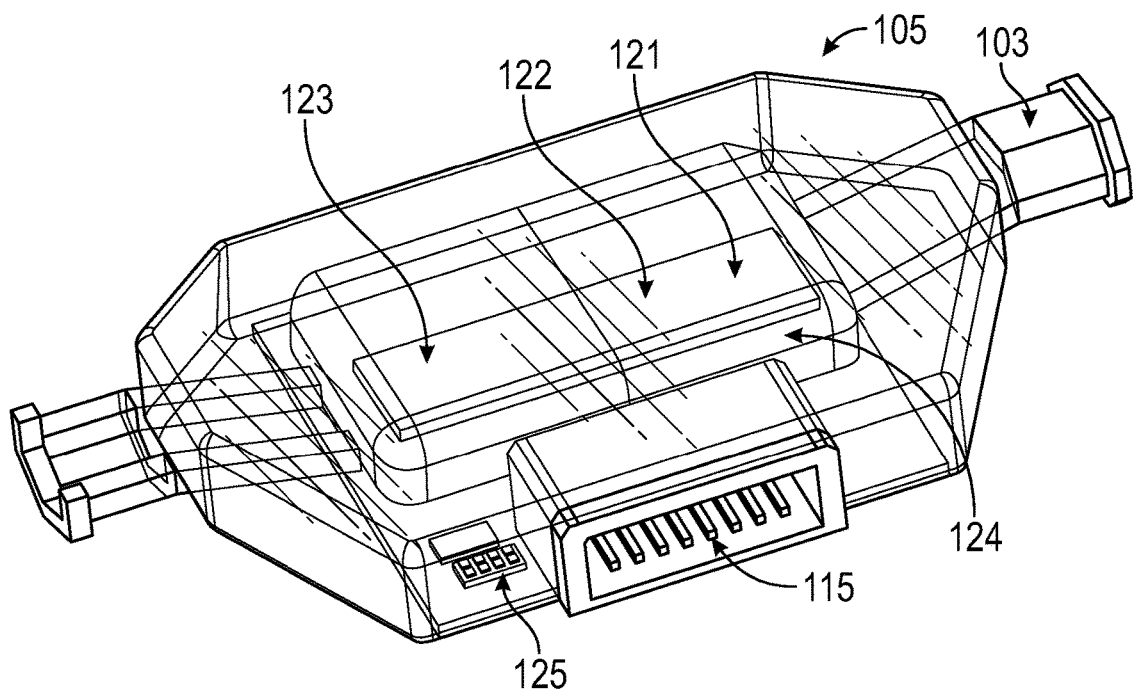
FIG. 2 is a schematic illustration of a sensor system for sensing indirect infection biomarkers, in accordance with an embodiment of the invention.

Reference is now made to FIG. 2, which is a schematic illustration of a sensor for sensing indirect infection biomarkers, in accordance with an embodiment of the invention. According to some embodiments, sensor system 105 may be used for the detection of indirect infection biomarkers, e.g., pH, lactic acid, exudate flow, fluid viscosity, local/systemic oxygen saturation, and local/systemic temperature. Further examples of indirect biomarkers may be immune-modulating mediators, such as IL-1, IL-6, IL-10 and TNF-α, pancreas enzymes such as amylase, inflammatory parameters such as Lipopolysaccharide Binding Protein (LBP), and metabolic parameters such as glucose. If sensor system 105 detects at least one of the above mentioned indirect infection biomarkers, it may indicate on presence and in some cases on the stage of infection.

Typically, a sensor for sensing indirect infection biomarker is located along tube 103, such to continuously detect changes occurring in level, or concentration, and so on, of the indirect biomarkers. In some embodiments, sensor system 105 may be located within drain tube 103 that is inserted into the patient thus having the advantage of sensor system 105 being closer to the surgical or wound site in order to monitor the presence of infection more closely. In other embodiments, sensor system 105 may be located along tube 103, thus having the advantage of monitoring only the contents of the flow of exudate leaving the surgical site, which may be more accurate compared to monitoring presence of infection in close proximity to the surgical site, since along tube 103 there is typically less noise from materials present in the surgical site following surgery, which may not be relevant to presence of bacteria. Sensor system 105 for sensing indirect infection biomarkers is typically not located within container 101, since if located within the container, sensor system 105 would not be able to detect continuous real-time changes of the level or concentration of the indirect biomarkers while these changes occur but rather sensor system 105 would only be able to detect accumulation of the indirect biomarkers, and this is less appropriate for the type of indirect infection biomarkers.

In some embodiments, sensor system 105 may comprise more than one sensor units for sensing presence, level or concentration of more than one type of indirect infection biomarker. For example, sensor system 105 may comprise sensor 123 for sensing pH (in some embodiments, sensor 123 may comprise more than one sensor for sensing pH, e.g., two or three sensors for sensing pH, in order to provide a more accurate detection), temperature sensor 121 used for pH adjustment and/or for sensing an additional indirect infection marker, i.e., temperature, and sensor 124 for sensing lactic acid. Other types of sensors and other combination of sensors may be incorporated as part of sensor system 105.

In some embodiments, sensor system 105 may be hollow in order to enable passage of drained fluids that pass through tube 103 to also pass through sensor system 105, thus enabling contact between the drained fluids and the at least one sensor implemented as part of sensor system 105. Each of the various sensors incorporated as part of sensor system 105 requires fluids to be in contact with the respective sensing elements, thus fluids drained through tube 103 are required to pass through sensor system 105 and to be in contact with the various sensing elements.

Temperature sensor 121 may sense the local increase of temperature by sensing the temperature of fluids drained from the surgery site through tube 103. When an infection begins, it may cause an increase in temperature, thus sensing changes in temperature may indicate on presence of infection.

pH sensor 123 may sense the level of pH of fluids drained from the surgery site through tube 103. pH sensor 123 may comprise more than one sensors for sensing pH in order to compare between detections of the plurality of pH sensors and thus enable a better and more precise determination of pH level. Typically, pH sensor 123 is combined with a temperature sensor for pH adjustment, since pH may be affected by temperature changes. When infection is present, the pH of the area of infection typically decreases as a consequence of the inflammation reaction and innate immunity activation by bacteria, which leads to the release of content by macrophage and neutrophil phagosomes. The intraphagosomal pH in macrophages progressively decreases to a pH level of 4-5, after 15 to 60 minutes from the beginning of inflammation. This acidification is important for bacterial killing. Neutrophil phagosomes are less acidic, and some studies even report a transient alkalization. Neutrophils and macrophages comprise the "front line" in trying to eliminate bacterial infection, operating at a very early stage. Therefore, by detecting a decrease in pH levels, an indication of the presence of infection may be made.

In some embodiments, pH sensor 123 may, for example, be an ion-sensitive field-effect transistor (ISFET) pH-sensor by Sentron Europe BV, The Netherlands, or pH microsensors or non-invasive pH sensors by PreSens—Precision Sensing GmbH, Germany, though other pH sensors may be incorporated in sensor system 105.

Lactic acid sensor 124 may sense the concentration of lactic acid in fluids that are drained from the surgery site by tube 103. Lactic acid is generated by different routes as a resultant of the metabolic consequences of endotoxins of Gram negative bacteria (e.g., *Pseudomonas* species, or Enterobacteriaceae). Endotoxins may cause vascular collapse and reduce tissue perfusion and oxygenation at the locally infected tissues, leading to increased lactate production. Lactic acid may also increase after the alteration in distribution and/or expression of lactic dehydrogenase isozymes, due to bacteria infection. Although lactic acid may also be generated in increased amounts due to other conditions such as acute illnesses (e.g., pyelonephritis, acute arteriosclerotic heart disease, acute pancreatitis, pneumonia, acute gastrointestinal bleeding, acute alcoholism, peritonitis, acute hepatitis, acute fatty metamorphosis of liver), an increase in concentration of lactic acid in local tissue fluids such as exsudates or cerebrospinal fluids is most often the consequence of bacteria infection. In presence of infection, lactic acid concentrations typically increase, thus if lactic acid sensor 124 senses an increase in lactic acid concentration, positive indication of the presence of infection may be made.

Other sensing units may be incorporated within sensor system 105. Some examples for additional sensing units may be of sensors for sensing viscosity, exudate levels or flow rate or exudate. The higher the viscosity and exudate levels or flow rate coming out from local tissue, i.e., tissue at the surgery site, the higher the chances are for presence of an infection. Wound exudate is generally defined as 'what is coming out of the wound', 'wound fluid', 'wound drainage' and 'an excess of normal fluid'. It is currently known that wound exudate is produced in response to a complicated interaction between wound aetiology, wound healing physiology, wound environment and compounding pathological processes. Exudate is derived from fluid that has leaked out of blood vessels and it closely resembles blood plasma. Fluid leaks from capillaries into body tissues at a rate that is determined by the permeability of the capillaries and the pressures (hydrostatic and osmotic) across the capillary walls. In a wound, the initial injury initiates inflammation, an early stage of the healing process. Mediators involved in inflammation, e.g., histamine released by mast cells, increase capillary permeability so that white blood cells can escape and the blood vessels leak more fluid. The excess fluid enters the wound where it forms the basis of the exudate. In a healing wound, exudate production generally reduces over time. However, in a wound that is not healing as expected, exudate production may continue and may be excessive due to ongoing inflammatory or other processes such as bacteria infection, which may fuel an exacerbated inflammation. Beyond the volume increase of exudate, the viscosity increase may also be indicative of bacteria infection and may be examined by a variety of sensors, comprising, for example, pressure sensors.

In some embodiments, sensor system 105 may comprise a pH sensor and a lactic acid sensor, or a pH sensor and a flow rate of exudate sensor, or a lactic acid sensor and a flow rate of exudate sensor or a pH sensor, a lactic acid sensor and a flow rate of exudate sensor. Other embodiments may comprise other combinations of pH, lactic acid and flow rate sensors along with other possible sensors, e.g., sensors for measuring temperature, sensors for measuring viscosity, sensors measuring oxygen saturation, and so on.

The temperature level detected by sensor 121 may (either prior to being transmitted to an external receiver, or after the detected signals are transmitted to an external receiver) be compared to a threshold. Such analysis of the detected signals of comparing the temperature level to a threshold enables not only a determination as to the presence of infection but also to a determination as to the stage of infection, whether mild, progressive or severe, and thus patient treatment may be modified and fitted accordingly. In some embodiments, sensor 121 may detect the rate of change of temperature, and said rate of change may be compared to a threshold, in order to determine the presence of infection.

According to some embodiments, each type of detected signals is compared to a different, respective threshold. In some embodiments, the threshold may either be a predetermined threshold or it may be an adjustable threshold, e.g., a threshold that may change according to the changing levels of biomarkers or may change according to the increase or decrease in the trend of sensed levels of biomarkers. An adjustable threshold may, for example, change depending on the time that had passed from surgery. That is, a certain threshold that may be adequate within a short time period post-surgery may no longer be relevant after a longer time period post-surgery. For example, if the sensor is for sensing pH, the threshold for determining presence of infection soon after surgery may be a pH of 7.1. If the sensor, e.g., sensor 123, senses a pH level lower than 7.1, a positive indication may be made as to presence of infection. However, several hours to days post-surgery, the threshold indicating presence of infection may be even lower than 7.1, and should be around 6.8. That is, if several hours or several days after surgery, the detected level of pH is 7.1, a definite indication as to presence of infection may not be made. However, if the sensed pH level is below 6.8, a positive indication as to presence of infection may be made. Other threshold levels of pH may be used.

In some embodiments, sensor system 105 may comprise a reference electrode or reference sensor 122 in order to serve as a reference to the various types of sensors, and thus a processor may compare the sensing signals of the various sensors to those of the reference signals, thereby determining whether or not the signals sensed by the sensors indeed indicate presence of infection. In some embodiments, following comparison between the signals sensed by the sensors to those sensed by the reference, an indication may be made as to the stage of infection, in addition to the presence of infection.

According to some embodiments, sensor system 105 may further comprise a memory unit 125 for recording the signals sensed by the sensing units in sensor system 105. Memory unit 125 may be an EEPROM (Electronically Erasable Programmable Read-Only Memory) or any other unit of the sort. In some embodiments, memory unit 125 may comprise a processor for processing the signals generated by sensor system 105. However, in other embodiments, memory unit 125 need not comprise a processor, and processing may be done in the external receiver (shown in FIG. 4).

In some embodiments, sensor system 105 may further comprise electrical contacts 115, which may be open to accept an electronic board, e.g., electronic board 106 (FIG. 1). As described with respect to FIG. 1, electronic board 106 may comprise a transmitter and antenna (not shown) that may transfer detections of presence of the biomarkers generated by sensor systems 105 to an external receiver (illustrated in system 200, FIG. 4). Electronic board 106 may comprise a power supply, e.g., at least one battery for supplying power to all of the electronic components within. Electronic board 106 may further comprise a processor for processing signals generated by sensor system 105 prior to the signals being transmitted to an external receiver. The processor within electronic board 106 may perform complete processing of the signals generated by the sensor system or the sensor units, such that the transmitted signals may be displayed to a user or may be used to generate a notification to the user with respect to presence of infection, and in some cases with respect to the stage of infection. In other embodiments, the processor may only perform initial processing on the signals generated by the sensors, and then the processed signals may be transmitted to an external receiver for further processing.

Figure 3:
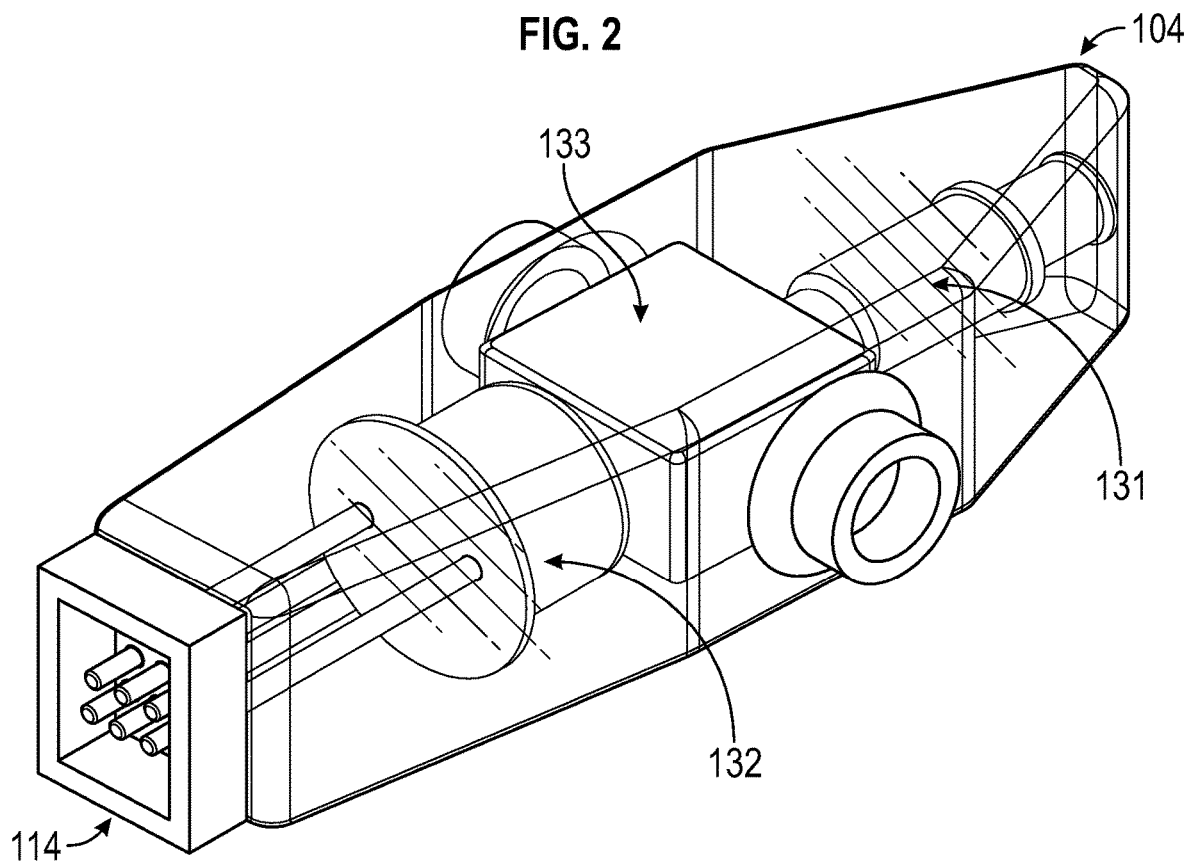
FIG. 3 is a schematic illustration of a sensor system for sensing direct infection biomarkers, in accordance with an embodiment of the present invention.

Reference is now made to FIG. 3, which is a schematic illustration of a sensor system for sensing direct infection biomarkers, in accordance with an embodiment of the present invention. According to some embodiments, sensor system 104 may be used for the detection of direct infection biomarkers, which include various types of bacteria, e.g., *Escherichia coli*, *Pseudomonas* spp including *Pseudomonas aeruginosa* and *Pseudomonas putida*, *Staphylococcus* spp including *Staphylococcus aureus*, *Streptococcus*, *Enterococcus*, *Serratia*, *Klebsiella*, *Morganella*, *Proteus* and Enterobacteriaceae.

In some embodiments, sensor system 104 may comprise sensor units, which may detect presence of volatile organic compounds. Such volatile organic compounds may serve as a signature of specific bacteria species or a group of bacteria species, e.g., sulfur compounds. That is, determining presence of various volatile organic compounds by at least one sensor, and analysing the signals generated by the sensor, may provide qualitative data, i.e., identification of presence of bacteria. In some embodiments, such analysis may further provide quantitative data, i.e., bacteria contamination or infection severity stage or level.

The gradual increase in bacteria concentration corresponds to the different stages of bacteria invasion into the surgery site. For example, the stage of colonization of bacteria may be generally expressed by values less than $10^2$ Colony Forming Units per milliliter [CFU/ml], the stage of contamination may be generally expressed by values between $10^2$ and $10^6$ [CFU/ml], and the stage of infection may be generally expressed by values above $10^6$ [CFU/ml]. Detecting $10^2$ [CFU/ml] by sensor system 104 may assist in diagnosing early infection stage prior to clinical observational signs of infection.

When the infection biomarker is a hemolytic bacteria specie (e.g., *S aureus*, hemolytic Streptococci, hemolytic *E. coli* subspecies, the stage of contamination may be generally expressed by values between $10^1$ and $10^4$ [CFU/ml], and the stage of infection may be generally expressed by values above $10^4$ [CFU/ml]. Detecting $10^1$ [CFU/ml] by sensor system 104 may assist in diagnosing early infection stage prior to clinical observational signs of infection.

In some embodiments, sensor system 104 may comprise a heating resistor for controlling the temperature of the chamber of sensor system 104 to be, for example, 30° C. or 37° C., for increasing the sensitivity level or the detection level of sensor system 104. Other temperature levels may be kept within the chamber of sensor system 104, while providing an optimal temperature for increasing the sensitivity level or the detection level of sensor system 104.

In some embodiments, sensor system 104 may comprise at least one opening 134 through which tube 103, which drains the fluids from the surgery site may pass, such that drained in-vivo fluids may be in contact with the sensing units within sensor system 104 and thus be examined for presence of bacteria that may indicate on presence of infection. In some embodiments, sensor system 104 may comprise at least one illumination source 131, e.g., an LED, for illuminating the in-vivo fluids that pass through tube 103. Sensor system 104 may further comprise a photodetector 132 for detecting illumination that passed from illumination source 131 and through the in-vivo fluids that pass through sensor system 104.

Sensor system 104 may further comprise a sol-gel material 133 or any other kind of materials that may capture bacteria within it, assuming bacteria is flowing within the in-vivo fluids drained from the surgery site. Sol-gel material 133 may refer to a material that is made of a gel-like network containing a liquid phase and a solid phase, typically comprising metal oxides, e.g., oxides of silicon and titanium. If bacteria is present within the fluids drained from the surgery site, while passing through tube 103 and through sensor system 104, such bacteria may be caught within material 133 and thus be illuminated by illumination source 131 and examined by photodetector 132. Sol-gel 133 may be located in between illumination source 131 and photodetector 132, such that light from illumination source 131 may illuminate sol-gel 133, may pass through sol-gel 133, and may reach photodetector 132. Changes in characteristics of light detected by photodetector 132 compared to the light irradiated from illumination source 131 may indicate on presence of bacteria, and even on concentration of bacteria present within sol-gel 133. Typically, sol-gel 133 may be located on the same axis along which illumination source 131 and photodetector 132 are located. In some embodiments, sol-gel 133 may be located at other locations, while ensuring that light from illumination source 131 may pass through sol-gel 133 and be detected by photodetector 132.

According to some embodiments, sensor system 104 may be designed to detect at least one type of bacteria. That is, sol-gel material 133 may be designed to capture at least one type of bacteria. However, according to other embodiments, sol-gel material 133 may be designed to capture more than one type of bacteria, and thus illumination source 131 may comprise more than one illumination source for illuminating and causing a reaction with the more than one type of bacteria. Furthermore, photodetector 132 may also be designed to detect light signals of more than one type of illumination source, such to enable detection of more than one type of bacteria. Since different bacteria may be activated or may change some characteristics of light of a certain wavelength, in order to detect more than one type of bacteria, illumination source 131 should comprise more than one type of illumination source, each illuminating at a different wavelength. Thus, photodetector 132 should be designed to detect those different wavelengths, following a possible reaction between light from each of the illumination sources and its corresponding bacteria.

According to some embodiments, sensor system 104 may be located within drain tube 103 where tube 103 is inserted into the surgical site, i.e., in close proximity to the surgical site, thus having the advantage of being closer to the surgical or wound site in order to monitor presence of infection more closely. In other embodiments, sensor system 104 may be located along tube 103, thus having the advantage of monitoring only the contents of the flow of exudate leaving the surgical site. However, in yet other embodiments, sensor system 104 may be located in container 101, thus having the advantage of sensing the overall concentration or level of the direct infection biomarkers, i.e., of the bacteria, and in some cases the overall rate of change of concentration or level of bacteria, which may be more accurate than any single discrete reading of exudate at a given instance. For direct infection biomarkers, i.e., for bacteria, monitoring accumulation of bacteria and thus monitoring concentration of bacteria compared to monitoring single discreet readings of presence of bacteria in exudate is more accurate and may help avoid "false" alarms in detection of the presence of infection.

Figure 4:
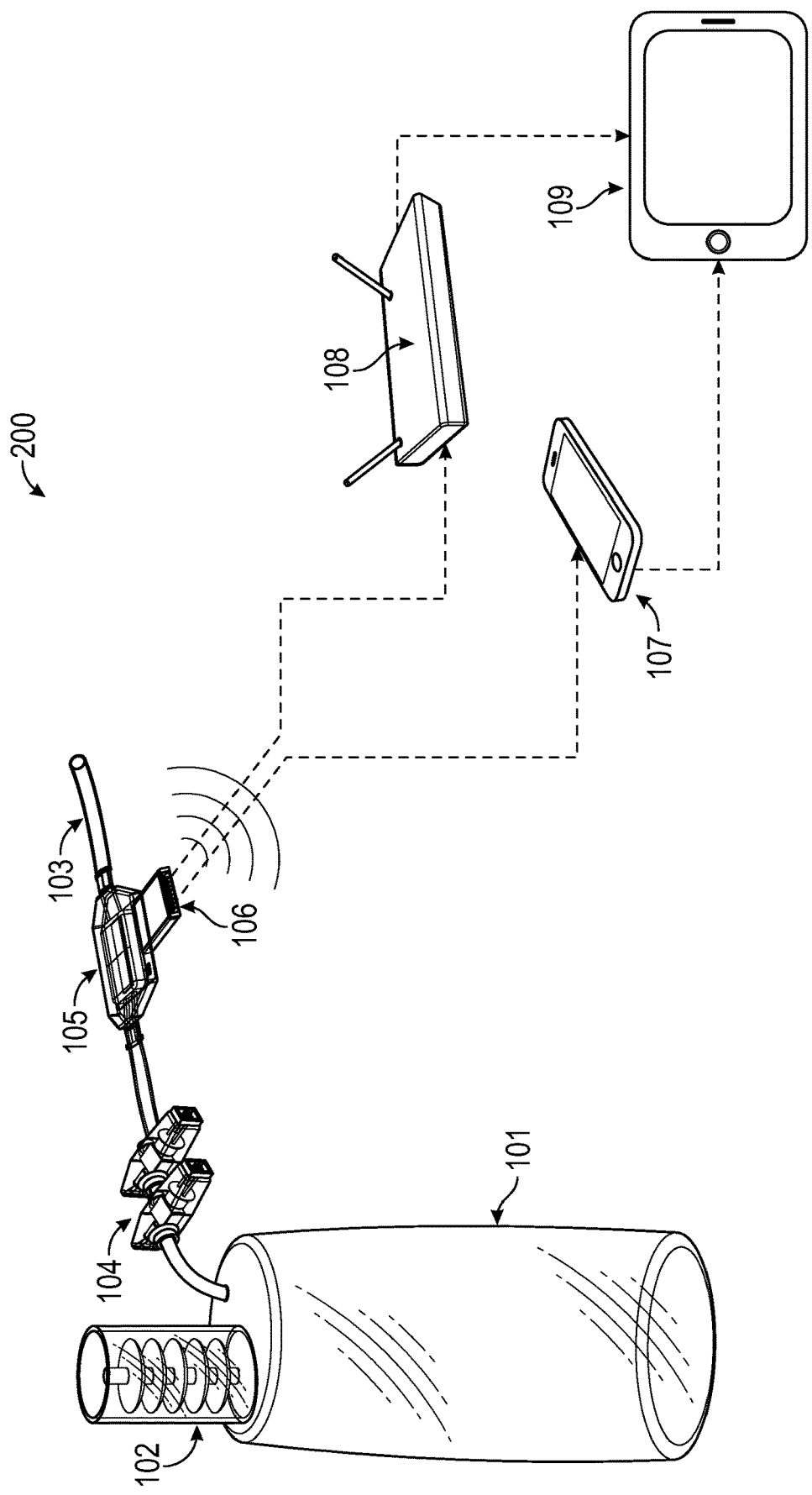
FIG. 4 is a schematic illustration of a drain system including a notification system, in accordance with an embodiment of the invention.

Reference is now made to FIG. 4, which is a schematic illustration of a drain system including a notification system, in accordance with an embodiment of the invention. System 200 may comprise a drain system comprising a drain tube 103 for draining exudate from the surgery site and into a container 101, where the exudate is accumulated. Container 101 may comprise a suction element 102, which may cause low or high pressure in order to actively suck fluids or exudate from the surgery site through tube 103 and into container 101. However, in other embodiments, drain system 100 need not comprise an active suction element 102, and drainage from the surgery site may operate passively. Also, in other embodiments, drain tube 103 need not drain fluids into a container but rather may be part of an open system, thereby draining fluids onto a dressing or something of the sort.

System 200 may further comprise at least one sensor system 104 for detecting direct infection biomarkers, and at least one sensor system 105 for detecting indirect infection biomarkers. Each of sensor systems 104 and 105 may comprise more than one sensor unit for detecting more than one type of an infection biomarker. In some embodiments, each of sensor systems 104 and/or 105 may be connected to an electronic board 106. Electronic board 106 may comprise a transmitter and antenna (not shown) that may transfer detections of the infection biomarkers done by sensor systems 104 and/or 105 to an external receiver. Typically, the transmission of data collected by both or either of sensor systems 104 or 105 may be wireless transmission, e.g., based on radio frequency, Bluetooth, Wireless Local Area Network (WLAN) or Wi-Fi, or any other kind of wireless transmission. According to some embodiments, the external receiver may either be a mobile device, e.g., mobile phone 107, which may receive the signals related to sensing presence of infection biomarkers generated by at least one sensor unit, through Bluetooth. According to other embodiments, the external receiver may be some kind of modem 108 for receiving the signals generated by at least one sensor unit through WLAN or Wi-Fi. Other types of receivers, typically wireless receivers may be used as part of system 200. In other embodiments, the external receiver may not be a wireless receiver but rather be a wired receiver; i.e., one that electronic board 106 may be connected to through wires and transmission of data may be done through physical wires. In some embodiments, the external receiver may comprise a processor for processing a signal generated by at least one sensor unit, which may be encapsulated by either of sensor systems 104 or 105. In other embodiments, the external receiver need not comprise a processor.

According to some embodiments, sensor systems 104 and/or 105 may communicate with remote devices 107 and 108 as described in U.S. Pat. No. 8,750,396, which is commonly owned by the assignee of the present application and is incorporated herein by reference in its entirety. In some embodiments, sensor systems 104 and/or 105 may transmit patient information to remote devices as described in U.S. patent application Ser. No. 13/942,225, which is commonly owned by the assignee of the present application and is incorporated herein by reference in its entirety.

In some embodiments, system 200 may further comprise a notification system 109. Notification system 109 may receive the detected data or signals from the external receiver for processing and for generating an indication as to the presence of an infection at the surgery site. Notification system 109 may comprise a processor for processing the signals generated by the sensor systems or sensor units. If external receiver 107 or 108, or even electronic board 106 comprises a processor, then notification system 109 need not necessarily comprise a processor. Notification system 109 may further comprise an analyzer for analyzing the processed signals by comparing the processed signals to a threshold. Each of the biomarkers, whether a direct infection biomarker or an indirect infection biomarker may have its own specific threshold to which the detected and processed signals are compared. After the analyzer compares the processed signals to a threshold, an indication may be generated as to the presence of infection at the surgical site. The indication as to presence of infection by system 109 may be made by generating some kind of alert noticed by the operator of system 200, e.g., a physician or a nurse or any other healthcare provider, or may be noticed by the patient who underwent the surgical operation. Various types of notifications may be generated by notification system 109, for example, a sound of some sort may be generated, a light source may be turned on or may change its color once presence of infection is determined, a literal indication may appear on a display unit, e.g., a screen of notification system 109, and so on.

According to some embodiments, notification system 109, and more specifically, the analyzer that is incorporated within notification system 109 may determine the presence of infection, as well as determine the stage of infection. Determining the stage of infection may correspond to determining whether the infection is at a first stage, a second stage or a third stage, and so on. Typically, the first stage of infection corresponds to a mild stage, e.g., the infection is at a very early stage and may not be detectable by typical monitoring; the second stage of infection may correspond to a progressive stage, e.g., the infection is progressing and is no longer in its initial mild stage; and the third stage may correspond to a severe stage of infection, e.g., the infection is at a critical stage and requires immediate treatment. Other definitions to the different stages of infection may be used.

In some embodiments, the thresholds to which the signals may be compared, may be predetermined prior to the beginning of the sensing or detecting procedure by the specific sensors. Yet, in other embodiments, the thresholds may be adaptive to changes in the sensed levels or concentration of the various infection biomarkers. Adaptive thresholds may mean that the analyzer may change the threshold's value based on changes in the sensed signals, or based on the analysis of the trend of the sensed signals. For example, if the biomarker is pH, and pH levels are initially low, soon after surgery, then an appropriate threshold may be lower than what a predetermined threshold would have been, and vice versa. An increase or decrease in the trend of sensed signals may be used to adjust the threshold according to which an indication of presence of infection as well as of the stage of infection may be generated. In some embodiments, the threshold may be based on the rate of change of the level or concentration of any infection biomarker. For example, if a rapid increase in the level or concentration of an infection biomarker is detected, the threshold value should be higher than what a predetermined threshold would have been without detecting the rate of change in the level or concentration of the infection biomarker. In the above example of a rapid increase in levels of the infection biomarker, one can assume there may be a leak from the in-vivo area that is being monitored, e.g., from the surgery site or from the GI tract, etc., which causes such an increased rate of change. Thus, the threshold requires adjustment such to avoid "false" alarms in the detection of infection.

For example, if the infection biomarker is pH, a first indication, which may correspond to a mild stage of infection, may be generated if the level of pH is equal to or below 7.1. That is, notification system 109 may generate a first indication as to presence of infection and as to the stage of infection, which is an initial and mild stage of infection if the level of pH sensed by the pH sensor (which may be part of sensor system 105) is equal to or below 7.1. In other embodiments, a different threshold may be used to which the sensed pH signals may be compared. A second indication, which may correspond to a progressive or severe stage of infection, may be generated if the level of pH is equal to or below 6.8. That is, notification system 109 may generate a second indication per presence of infection as well as the stage of infection being progressive or severe, if the signals detected by the pH sensor are equal to or below 6.8. Other thresholds for such a second indication, indicating a more progressed stage or level of infection may be used.

Furthermore, if the infection biomarker is pH, the threshold according to which indications on the presence (and level) of infection may be made, may be based on the rate of change of the level of pH, which is typically a decrease in case of an infection. For example, a first indication, which may correspond to a mild stage of infection, may be generated if the mean decrease rate is above 0.1 [pH unit/hour] for longer than 1 hour. A second indication, which may correspond to a progressive stage of infection, may be generated if the mean decrease rate is above 0.1 [pH unit/hour] for more than 3 hours. A third indication, which may correspond to a severe stage of infection, may be generated if the mean decrease rate is above 0.1 [pH unit/hour] for more than 6 hours. In another example, if the mean decrease rate is above 0.2 [pH unit/hour] for more than 1 hour, a second indication, which may correspond to a progressive stage of infection, may be generated. In other embodiments, other mean decrease rates and/or other time lines may be chosen.

In other examples, the threshold according to which indications on the presence (and level) of infection may be made, may be based on the total time that a pH level stays substantially unchangeable with respect to a threshold/baseline level. For example, a first indication, which may correspond to a mild stage of infection, may be generated if the total time of pH level being below the baseline, e.g., below 7.1, is longer than 1 hour. A second indication, which may correspond to a progressive stage of infection, may be generated if the total time of pH level being below the baseline of e.g., 7.1, is longer than 3 hours. A third indication, which may correspond to a severe stage of infection, may be generated if the total time of pH level being below the baseline, e.g., below 7.1, is longer than 6 hours. In other embodiments, other time lines and/or other thresholds or baselines may be chosen.

In case the biomarker is lactic acid, a first indication, which may correspond to a mild stage of infection, may, for example, be generated by notification system 109 during the first hour post-surgery (or so), if the concentration of lactic acid is equal to or above a threshold of 3 [mM]. Such an indication may indicate presence of infection, and yet further indicate on the stage of infection being mild, thus detecting early signs of post-surgery. In other embodiments, the threshold to which the concentration of lactic acid that is sensed, e.g., by sensor system 105, may be compared to, may be different than 3 [mM]. In other embodiments, the analyzer within notification system 109 may compare the sensed concentration of lactic acid to a different threshold. Typically, the appropriate threshold may be predetermined according to experiments examining the changes in lactic acid concentration that are typical to early stages of infection. In some embodiments, the threshold need not be predetermined but may rather be an adaptive threshold, which may change according to initial level of concentration of lactic acid soon after surgery, or according to the slope of change of lactic acid concentration during a few periodic sensing events by, e.g., sensor system 105.

A second indication, which may correspond to a progressive stage of infection, may, for example, be generated by notification system 109 if the concentration of lactic acid is above the threshold for 6 hours after the first indication. That is, if the sensed concentration level of lactic acid is still above the threshold of 3 [mM] for 6 hours after the first indication, the analyzer that is included in notification system 109, which compares the sensed concentration level to the threshold, may generate a notification that not only is there presence of infection but also that the infection is in progressive stage. A third indication, which may correspond to a severe stage of infection, may, for example, be generated if the concentration of lactic acid is above the threshold for 24 hours after the first indication. The analyzer within notification system 109 may compare the sensed concentration of lactic acid to the threshold of 3 [mM] and if the sensed concentration is above the threshold for 24 hours after the first indication, then the analyzer may generate an indication and notification of presence of an infection as well as on the stage of infection being severe. Once the care provider is notified on the stage of the infection in the surgery site, let alone the presence of infection, the care provider may use the most appropriate means (e.g., medicaments) in treating such an infection. Other timelines and other thresholds may be used for generating any of the indications mentioned above.

Furthermore, if the infection biomarker is lactic acid, the threshold according to which indications on the presence (and level) of infection may be made, may be based on the rate of change of the level of lactic acid, which is typically an increase in case of an infection. For example, a first indication, which may correspond to a mild stage of infection, may be generated if the mean increase rate is above 0.1 [mM/hr] for more than 1 hour post-surgery. A second indication, which may correspond to a progressive stage of infection, may be generated if the mean increase rate is above 0.1 [mM/hr] for more than 3 hours post-surgery. A third indication, which may correspond to a severe stage of infection, may be generated if the mean increase rate is above 0.1 [mM/hr] for more than 6 hours post-surgery. In another example, if the mean increase rate is above 0.2 [mM/hr] for more than 1 hour post-surgery, a second indication, which may correspond to a progressive stage of infection, may be generated. In other embodiments, other mean increase rates and/or other time lines may be chosen.

In other examples, the threshold according to which indications on the presence (and level) of infection may be made, may be based on the total time that lactic acid level stays substantially unchangeable with respect to a threshold/baseline level. For example, a first indication, which may correspond to a mild stage of infection, may be generated if the total time that concentration of lactic acid stays above the baseline, e.g., above 3 [mM], is longer than 1 hour. A second indication, which may correspond to a progressive stage of infection, may be generated if the total time that concentration of lactic acid stays above the baseline, e.g., above 3 [mM], is longer than 3 hours. A third indication, which may correspond to a severe stage of infection, may be generated if the total time that concentration of lactic acid stays above the baseline, e.g., above 3 [mM], is longer than 6 hours. In other embodiments, other time lines and/or other thresholds or baselines may be chosen.

In case the infection biomarker is a flow rate of exudate coming out of the surgery site, a first indication, which may correspond to a mild stage of infection, may, for example, be generated by notification system 109, 6 hours post-surgery if the flow rate is above 5 milliliter per hour [ml/hr]. The analyzer within notification system 109 may compare the flow rate sensed by sensor system 105, to the threshold of 5 [ml/hr] 6 hours post-surgery. If the sensed flow rate exceeds the threshold of 5 [ml/hr], then the analyzer and thus notification system 109 may generate an indication or alert not only of the presence of infection but also of the stage of infection being mild. The value of the threshold may be different than 5 [ml/hr], while being indicative of a mild stage of infection, thus detecting early signs of post-surgery. The threshold value may be predetermined based on experiments examining behavior and characteristics of an infection in a surgical site. In other embodiments, the threshold may not be predetermined but rather may change in accordance with changes in the sensed flow rate. For example, if the initial flow rate is already close to the threshold value, notification system 109 may adjust the threshold value to be different than the initially chosen threshold. Furthermore, the threshold may change while corresponding to the changes in sensed values of flow rate.

A second indication, which may correspond to a progressive stage of infection, may, for example, be generated 6 hours post-surgery if the flow rate is above 10 [ml/hr]. If the sensed flow rate exceeds the new threshold of 10 [ml/hr] following 6 hours from surgery, then the analyzer or notification system 109 may generate an indication not only of the presence of infection but also of the stage of infection being progressive. Other threshold values and other timings may be selected. In some embodiments, the threshold value may be adaptive or changeable such to correspond to changes in the sensed parameters.

A third indication, which may correspond to a severe stage of infection, may, for example, be generated 6 hours post-surgery if the flow rate is above 20 [ml/hr]. notification system 109 may generate an indication to the presence of infection as well as to the stage of infection being severe, if following 6 hours from surgery, the flow rate sensed by sensor system 105 exceeds 20 [ml/hr]. Other threshold values and other timings may be selected. In some embodiments, the threshold value may be adaptive or changeable such to correspond to changes of the sensed parameters.

In case the infection biomarkers are immune-modulating mediators, such as IL-1, IL-6, IL-10 and TNFα; a first indication may be generated if the level of at least one of these mediators is above 100% of a baseline/threshold value. In some embodiments, the baseline value may be obtained during the surgery or from the very first fractions of the collected exudates. A second indication may be generated if the level of at least one of these mediators is above 200% of the baseline value, or if the level of at least two of these mediators is above 100% of the baseline value, or if such levels are observed with an increasing trend over at least two consecutive measurements within intervals in the range of 4 to 24 hours.

In case the infection biomarker is LBP; a first indication may be generated if the level of LBP is above 100% of a baseline value. In some embodiments, the baseline value may be obtained during the surgery or from the very first fractions of the collected exudates. A second indication may be generated if the level of LBP is above 200% of the baseline value, or if the level of LBP is observed with an increasing trend over at least two consecutive measurements within intervals in the range of 4 to 24 hours. When said biomarker is glucose; a first indication may be generated if the level of glucose is below at least 20% of a normal value (indicatively 8 [mmol/l]), and with a decreasing trend during at least a day, while a second indication may be generated if the level of glucose is below 30% of the baseline/normal value with a decreasing trend during at least 2 days. When said biomarker is amylase; a first indication may be generated if the level of amylase is above 100 U/l, before the first 24 hours post-surgery, while a second indication may be generated if such level of amylase of above 100 U/l is observed over at least two consecutive measurements within intervals in the range of 4 to 24 hours.

In case the biomarker is a direct infection biomarker, i.e., bacteria specie, the biomarker may be selected from the group consisting of: *Escherichia coli, Pseudomonas* spp., *Pseudomonas aeruginosa, Pseudomonas putida, Staphylococcus* spp., *Staphylococcus aureus, Staphylococcus epidermidis, Streptococcus* spp., *Enterococcus* spp., *Klebsiella* spp., *Proteus* spp., *Serratia* spp., *Morganella* spp. and other Enterobacteriaceae, or a combination thereof. When the infection biomarker is a non-hemolytic bacteria specie, a first indication, which may correspond to a mild stage of infection, may, for example, be generated by notification system 109 if Colony Forming Units (CFU) is above $10^2$ [CFU/ml]. That is, if the number of colony units formed following surgery exceeds $10^2$ per milliliter, then notification system 109 may generate an indication of presence of infection and of the stage of infection being mild. A second indication, which may correspond to a progressive stage of infection, may, for example, be generated by notification system 109 if CFU is above $10^3$ [CFU/ml]. A third indication, which may correspond to a severe stage of infection, may, for example, be generated by notification system 109 if CFU is above $10^4$ [CFU/ml]. Other threshold values and other timings may be selected. In some embodiments, the threshold value may be adaptive or changeable such to correspond to changes of the sensed parameters.

When the infection biomarker is a hemolytic bacteria specie (e.g., *S aureus*, hemolytic Streptococci, and hemolytic *E. coli* subspecies), a first indication which may correspond to a mild stage of infection, may be generated if Colony Forming Units (CFU) is above $10^1$ [CFU/ml], a second indication, which may correspond to a progressive stage of infection, may be generated if CFU is above $10^2$ [CFU/ml], and a third indication, which may correspond to a severe stage of infection, may be generated if CFU is above $10^3$ [CFU/ml].

In some embodiments, the readings or sensing of presence of any direct infection biomarker, should take place at least every increase of 1 Log of CFU. An increase of 0.3 Log of CFU is substantially equivalent to one doubling time of bacteria, thus readings of presence of bacteria should typically be done every two doubling times. Some examples for doubling times for various bacteria may be as follows:

for *Klebsiella* spp, *Proteus* spp, *Serratia, Morganella*, and *E coli* type bacteria, doubling time may be every 20 to 45 minutes;

for *Pseudomonas* type bacteria, doubling time may be every 30 to 40 minutes;

for *Staphylococcus* type bacteria, doubling time may be every 20 to 30 minutes; and for *Streptococcus* type bacteria, doubling time may be every 20 to 30 minutes.

Accordingly, for *Pseudomonas* type bacteria, sensing of presence of these bacteria should be done at least every one hour.

In some embodiments, in case the doubling time of a certain bacteria is quicker than the doubling time mentioned above with respect to the various types of bacteria, then an indication that may correspond to a more progressive stage of infection may be generated, compared to the indication that would have been generated if the doubling time was similar to those mentioned above. For example, if the biomarker is *S. aureus*, which is Staphylococci and a hemolytic type bacteria, a detection of $10^2$ [CFU/ml] may generate a second alert level, as mentioned above. However, if the doubling time of *S. aureus* is less than 20 minutes, which is the typical doubling time for *Streptococcus* type bacteria, this may cause an indication that may correspond to a higher stage of infection, e.g., a severe stage of infection.

In some embodiments, the infection biomarker may be temperature. However, more important than measuring the discrete level of temperature, is measuring the rate of change of temperature, since the rate of change of temperature is a good indication on the presence of infection. The higher the rate of change in temperature is, the more progressed the infection is. For example, a first indication, which may correspond to a mild stage of infection, may, for example, be generated by notification system 109 if a rate of change in temperature is 0.5 [° C./hr], and a second indication, which may correspond to a progressive or severe stage of infection, may be generated if a rate of change in temperature is 1° C./hr.

In some embodiments, there may be additional biomarkers for early infection diagnosis, for example, Group A may comprise the following biomarkers: RANTES (Regulated on Activation, Normal T cell Expressed and Secreted) Osteopontin, or Macrophage migration inhibitory factors (MIP)—e.g., MIP-1, MIP-1a, MIP-1b, MIP-2 and, IL-2I. A first indication may be generated if the level of at least one of the mediators/biomarkers mentioned in Group A is greater than two times the baseline value. The baseline/initial value may be obtained during surgery or from the very first fractions of the collected exudates, or alternatively, according to the mean or median values observed in healthy patients. A second indication may be generated if the level of at least one of these mediators is greater than three and a half times the baseline value or if at least one of these mediators is combined with at least one biomarker selected from all of the above mentioned biomarkers (with respect to the biomarkers disclosed in the description of FIGS. 1, 2, 3 and 4), which generated a first indication level or if such levels are observed with an increasing trend over at least two consecutive measurements within intervals in the range of 4 to 24 hours.

Additional biomarkers may comprise other inflammatory markers IL-1β, and IL-8. A first indication on presence of infection may be generated if the level of at least one of these biomarkers is greater than three times the baseline/initial value (the initial value may be obtained during surgery or from the very first fractions of the collected exudates, or alternatively according to the mean or median values observed in healthy patients). A second indication on presence of infection may be generated if the level of at least one of these biomarkers is greater than five times the baseline value or if at least one of these biomarkers is combined with at least one biomarker selected from all of the above mentioned biomarkers (with respect to the biomarkers disclosed in the description of FIGS. 1, 2, 3, and 4), which generated a first indication level or if such levels are observed with an increasing trend over at least two consecutive measurements within intervals in the range of 4 to 24 hours.

Other examples of biomarkers from Group A may comprise additional inflammatory markers, Monocyte chemotactic proteins, e.g., MCP-1, and MCP-2. A first indication on presence of infection may be generated if the level of at least one of these biomarkers is greater than two times a baseline value (the initial/baseline value may be obtained during surgery or from the very first fractions of the collected exudates, or alternatively according to the mean or median values observed in healthy patients). A second indication may be generated if the level of at least one of these mediators/biomarkers is greater than five times the baseline value or if at least one of these mediators is combined with at least one biomarker selected from all of the above mentioned biomarkers (with respect to the biomarkers disclosed in the description of FIGS. 1, 2, 3, and 4), which generated a first indication level or if such levels are observed with an increasing trend over at least two consecutive measurements within intervals in the range of 4 to 24 hours.

Further examples of biomarkers from Group A may comprise additional inflammatory markers IL-17, IL-18, and IL-27. A first indication on presence of infection may be generated if the level of at least one of these biomarkers is below 80% of a baseline value (the baseline/initial value may be obtained during surgery or from the very first fractions of the collected exudates, or alternatively according to the mean or median values observed in healthy patients). A second indication may be generated if the level of at least one of these biomarkers is below 66% of the baseline value or if at least one of these biomarkers is combined with at least one biomarker selected from all of the above mentioned biomarkers (with respect to the biomarkers disclosed in the description of FIGS. 1, 2, 3, and 4), which generated a first indication level or if such levels are observed with increasing or decreasing trends over at least two consecutive measurements within intervals in the range of 4 to 24 hours, according to the trend of biomarkers for infection diagnosis.

In some embodiments, there may be additional biomarkers for early infection diagnosis, for example, Group B may comprise biomarkers with procoagulant or anticoagulant activities. The biomarkers of Group B should preferably be monitored during the first post-operative day (i.e., the first day following surgery), when the exudates typically contain substantial amounts of blood. Examples of such biomarkers may be Antithrombin III, Protein C, and Protein S. A first indication on presence of infection may be generated if the level of at least one of these biomarkers is below 80% of a baseline value (the baseline value may be obtained during the surgery or from the very first fractions of the collected exudates, or alternatively according to the mean or median values observed in healthy patients). A second indication may be generated if the level of at least one of these mediators/biomarkers is below 66% of the baseline value or if at least one of these sub-group biomarkers from Group B is combined with at least one biomarker selected from all of the above mentioned biomarkers (with respect to the biomarkers disclosed in the description of FIGS. 1, 2, 3, and 4), which generated a first indication level or if such levels are observed with increasing or decreasing trends over at least two consecutive measurements within intervals in the range of 4 to 24 hours, according to the trend of biomarkers for infection diagnosis.

Other examples of biomarkers from Group B may comprise F1.2, and Thrombomodulin. A first indication on presence of infection may be generated if the level of at least one of these mediators is greater than one and a half times a baseline value (the baseline value may be obtained during surgery or from the very first fractions of the collected exudates, or alternatively according to the mean or median values observed in healthy patients). A second indication on presence of infection may be generated if the level of at least one of these mediators is greater than two and a half times the baseline value or if at least one of these sub-group of biomarkers from Group B is combined with at least one biomarker selected from all of the above mentioned biomarkers (with respect to the biomarkers disclosed in the description of FIGS. 1, 2, 3, and 4), which generated a first indication level or if such levels are observed with an increasing trend over at least two consecutive measurements within intervals in the range of 4 to 24 hours.

Another example for a coagulation biomarker from Group B is D-Dimer. A first indication on presence of infection may be generated if the level of at least one of these mediators is greater than five times a baseline value (the initial/baseline value may be obtained during surgery or from the very first fractions of the collected exudates, or alternatively according to the mean or median values observed in healthy patients). A second indication may be generated if the level of at least one of these mediators is greater than ten times the baseline value or if at least one of these sub-group of biomarkers from Group B is combined with at least one biomarker selected from all of the above mentioned biomarkers (with respect to the biomarkers disclosed in the description of FIGS. 1, 2, 3, and 4), which generated a first indication level or if such levels are observed with an increasing trend over at least two consecutive measurements within intervals in the range of 4 to 24 hrs.

Yet a further example of biomarkers of Group B may comprise Platelet Factor 4, Plasminogen activator inhibitor, TAT, and cross-linked fibrin. A first indication on presence of infection may be generated if the level of at least one of these biomarkers is greater than two times the baseline value (the baseline/initial value may be obtained during surgery or from the very first fractions of the collected exudates, or alternatively according to the mean or median values observed in healthy patients). A second indication may be generated if the level of at least one of these mediators is greater than three and a half times the baseline value or if at least one of these sub-group of biomarkers from Group B is combined with at least one biomarker selected from all of the above mentioned biomarkers (with respect to the biomarkers disclosed in the description of FIGS. 1, 2, 3, and 4), which generated a first indication level if such levels are observed with an increasing trend over at least two consecutive measurements within intervals in the range of 4 to 24 hours.

In some embodiments, there may be additional miscellaneous biomarkers for early infection diagnosis, for example, Group C may comprise cell receptor type markers, such as: CC chemokine receptor (CCR), CCR 3, C5L2, CRTh2, Soluble Fas receptor (soluble), Fc-gamma RIII, soluble FLT-1, GP130, soluble IL-2 receptor, soluble phospholipase A2 including Group II (PLA2-II), soluble RAGE, soluble ST2 (IL-1 receptor), Toll-like receptor (TLR) 2, TLR 4, Transient receptor potential vanilloid, (TRPV)1, soluble TREM-1, soluble TNF-receptor, soluble Urokinase type plasminogen activator receptor (uPAR), ADAMTS-13, Angiopoietin—e.g. Angiopoietin-1, Angiopioetin-2—, Endothelial leukocyte adhesion molecule (ELAM)-1, Endothelial progenitor cells (cEPC), Endocan, Endothelin-1, soluble Intracellular adhesion molecule (ICAM)-1, Laminin, Neopterin, Platelet-derived growth factor (PDGF)-BB, E-Selectin, Soluble L-Selectin, P-Selectin, Vascular cell adhesion molecule (VCAM)-1, Vascular endothelial growth factor (VEGF), von Willebrand factor and antigen, Adrenomedullin, Proadrenomedullin, Anandamide, Angiotensin converting enzyme (ACE), 2-arachidonoylglycerol, Copeptin, C-type natriuretic peptide (CNP), Cycling nucleotides, Elastin, cGRP, 47 kD HK, Neuropeptide Y, Nitric oxide (NO), nitrate, nitrite, Substance P, Tetrahydrobiopterin, Vasoactive intestinal peptide (VIP), Serum amyloid A (SAA), Ceruloplasmin, C-reactive protein (CRP), Ferritin, Alpha1-acid glycoprotein, Hepcidin, Procalcitonin, Pentraxin 3, Atrial natriuretic peptide (ANP), Brain natriuretic peptide (BNP), Carbomyl phosphate synthase (CPS)-, Endothelin-1, pro-endothelin-1, Filterable cardiodepressant substance (FCS), Gc-globulin, Glial fibrillary acidic protein (GFAP), alpha glutathione S-transferase (GST), Hepatocyte growth factor (HGF), MEGX test, Myocardial angiotensin II, NSE, Pancreatitis-associated protein-I, Pre B cell colony-enhancing factor (PBEF), Protein S-100b, Surfactant protein—e.g. Surfactant protein A, Surfactant protein B, Surfactant protein C, Surfactant protein D, Troponin, Alpha2 macroglobulin, Albumin, Anti-endotoxin core antibodies (EndoCab), Apolipoprotein Cl, Bcl-2, Beta-thromboglobulin, Caspase-1, Ceramide, Cholesterol, Complement factors—e.g. C3, C4, C5a —, Terminal complement complex, Dendritic cell, Dipeptidylpeptidase, Diiodotyrosine (DIT), Eicosanoid, Elastase, Elastase, a1-antitrypsin complex, Erythropoietin, F2, Fatty acid amide hydrolase, Free DNA, G-CSF, GM-CSF, Gelsolin, Ghrelin, Growth arrest specific protein (Gas), Heat shock proteins (HSP)—e.g. HSP 70, HSP 72, HSP 73, HSP 90, HSP 32—, HDL cholesterol, soluble HLA-G5 protein, H2S, Hyaluronan, Hydrolytic IgG antibodies, Inter-alpha inhibitor proteins (IalphaIp), Intracellular nitric oxide in leukocyte, IP-10, Lactoferrin, Leptin, Serum lysozyme, Matrix-metalloproteinases (MMP)—e.g. MMP-2, MMP-9, MMP-1, MMP-8, MMP-13, MMP-7, MMP-3, MMP-10—, Neurotensin, Nociceptin, Orphanin FQ, NF-kB, Nucleosomes, Peptidoglycan, Amino-acids, Fibronectin, Plasmin alpha2-antiplasmin complex, Renin, Resistin, Selenium, Selenoprotein P, Bicarbonate, Sphingomyelinase, Sulfite, Transforming growth factor (TGF)—e.g. TGF-b, Tissue Inhibitor of Metalloproteinases (TIMP)—e.g. TIMP-1, TIMP-2, TIMP-3, Uric acid, Annexin V binding, Xanthine oxidase, soluble CD11b, Heparin Binding Protein (HPB), soluble receptor of advanced glycation end-products (RAGE), IL-10, IL-13, GM-CSF, IP-10, IFNg, IL-1a, GP130, IL-2 receptor, Fas, TNF-Receptor 1, and TNF-Receptor 2.

In some embodiments, Biomarkers from Group A are less accurate in being indicative of presence of infection compared to the biomarkers listed with respect to FIGS. 1, 2, 3, and 4. However, the biomarkers listed as part of Group A may still provide information on the presence of infection, with or without the biomarkers listed in FIGS. 1, to 4. Biomarkers from Group B are a bit less preferable than those in Group A, and biomarkers from Group C are less preferable than those in Group B. However, biomarkers from any of groups A, B or C may be used either alone, in any combination with other biomarkers from groups A, B or C, in combination with biomarkers listed with respect to FIGS. 1-4 or without such combination, in order to provide information on the presence of infection.

In some embodiments, all the disclosed biomarkers (those listed in FIGS. 1-4, Group A, Group B, and Group C) may be combined with cell analysis for early infection diagnosis, since changes in cell formulation may be indicative of infection events. Preferably, analysis of cells, which are involved in the inflammatory reaction and/or infection, e.g., neutrophils, mast cells, basophils, eosinophils, mononuclear cells (i.e., monocytes, macrophages), and lymphocytes, and more preferably analysis of neutrophils, macrophages and lymphocytes, may be combined with detection of at least one of the biomarkers listed above. In some embodiments, the analysis of macrophages may be carried out at the level of subtypes, for example, classically activated macrophages, or M1 and macrophages, and alternatively activated or M2, alternatively, LPS/IFNγ activated macrophages and IL-4 activated macrophages. In some embodiments, the analysis of lymphocytes may be carried out at the level of subtypes, for example, innate immune cells, including Natural Killer cells, TH1 CD4+ cells and CD8+ cytotoxic T lymphocytes. These analyses may comprise the use of immuno-assays, for a combination of cell surface markers, for example, clusters of differentiation (CD)—e.g., MHC class I, CD4, CD8 [T Lymphocyte], CD14, CD33, CD86, CD206, CD56 [Natural Killer], CD66b [Granulocytes, Neutrophils], and CD64. The analyses may comprise identification of cell types derived from the analysis of specific single cell surface markers or a combination of cell surface markers; more preferably cell subtypes, as mentioned above. A first indication on presence of infection may be generated if there is a persisting increase trend of at least 50% above baseline values, for any one of the above mentioned cells, in intervals within the range of 4 to 24 hours. In some embodiments, the examination and determination of the increasing trend should preferably be done during the first few days post-surgery.

In some embodiments, as described above, the stages of infection defined as mild, progressive, and severe, may correspond to a first indication of infection, a second indication of infection, and a third indication of infection, respectively.

In some embodiments, other stages besides mild, progressive or severe may be defined by the user or operator of system 200, according to which a notification of presence and stage or level of infection may be generated.

In some embodiments, system 200 may comprise more than one type of biomarkers, either more than one type of indirect biomarker, or more than one type of direct biomarkers, or a combination of at least one direct biomarker and at least one indirect biomarker. When system 200 comprises more than one type of biomarker, a combined threshold that takes into consideration the plurality of types of biomarkers may be one according to which a notification as to presence of infection as well as the stage of infection may be generated by notification system 109. For example, system 200 may comprise one sensor unit for detecting the level of pH and another sensor for detecting concentration of lactic acid, such that the biomarkers that system 200 is required to detect are pH and lactic acid. If the analyzer within notification system 109 records pH below or equal to 7.1, and lactic acid concentration increase of 0.1 [mM/hr] for more than 1 hour, then notification system 109 may generate an indication or alert referring not to a first stage of infection being mild, but rather to a second indication, which may correspond to a progressive stage of infection. That is, if each of the biomarkers were detected alone, notification system 109 would have generated a first indication of presence of infection, and one which may correspond to a mild stage of infection. Whereas, when more than one type of biomarker is detected by system 200 and each of the biomarkers exceeds their corresponding threshold, it may be concluded that the stage of infection is in fact more progressed, thus notification system 109 may generate a second indication, which may correspond to a progressive stage of infection. It seems that when system 200 comprises sensors for sensing more than one type of biomarkers, system 200 may be more accurate, not only as per presence of infection, but also as per the stage of infection.

According to some embodiments, each of the sensor units or sensor systems within system 200 may sense presence of its corresponding infection biomarkers continuously, e.g., the sensors may be activated without stopping. In other embodiments, each of the sensors may sense the presence of their corresponding infection biomarkers periodically, e.g., every few minutes. For example, metabolism modifications are quite rapid. Thus, pH that drops due to degranulation of polymorphonuclear cells and macrophages may be observed in less than 1 minute. Changes in lactic acid concentration may take more time, e.g., approximately less than 5 minutes. Flow rate of exudates may be even more gradual, e.g., may change in less than 15 minutes. Thus, if a sensor is to sense presence of pH, the sensor should sense the levels of pH, if not continuously, then at least within periods of time that are shorter than 1 minute. If the sensor is to sense concentration of lactic acid, the sensor should sense the concentration, if not continuously, then at least within periods of time shorter than 5 minutes. And if sensor is to sense flow rate of exudates, the sensor should sense the flow rate if not continuously then at least within periods of time shorter than 15 minutes.

If system 200 is to sense presence of direct infection biomarkers, i.e., bacteria specie, then the sensor should sense the formation of bacteria colonies continuously, and if not continuously then periodically within time periods shorter than 10 minutes.

In some embodiments, The correlation between a combination of any listed markers and post-operative infection may be analyzed by multivariate analysis, by using bespoke statistical and mathematical models (i.e., using such models per each particular person/patient), for example, Chain Model, Bayesian Models, logistic regression, canonical correlation analysis, principal component analysis, or any other model of the sort. Using statistical and mathematical models, as described above, may provide access to average and standard deviations thus providing estimates and margins of error, and provide access to correlations thus providing quantifying relationships between pairs of variables. The correlation coefficients may measure the strength of the linear association between numerical variables. In some embodiments, prediction ellipses in scatter plots as a visual test for bivariate normality can also give an indication of the strength of the correlation.

In some embodiments, the use of bespoke statistical and mathematical models may help predict the likelihood of early post-operative infection with associated probability of post-operative infection certainty. The level of alert may then be generated by the level of probability of confirmed early diagnosis of post-operative infection.

In some embodiments, early diagnosis of complications may further be refined by associating the combination of infection biomarkers with patient's data, for example, from the Electronic Medical Record (EMR), the Electronic Health Record (EHR). This may ultimately lead to the implementation of clinical algorithms for analyzing the correlation between post-operative infection and the combination of markers completed with various attributes of a particular patient's medical data, by using big data analytics such as data collection (data mining), data analysis, statistical analysis, predictive modelling and predictive model deployment. Depending on the complexity of the data and the availability of the data sets, machine learning algorithms may also be explored in order to improve the correlation analysis.

In some embodiments, the use of bespoke data analytics may help predict the likelihood of early post-operative infection with associated probability of post-operative infection certainty from the combination of infection biomarkers and patient medical data, for each particular patient. The level of alert may then be generated by the level of probability of confirmed early diagnosis of post-operative infection. For example, a first level of alert may be generated if probability of post-operative infection is equal or higher than 50%; a second level of alert may be generated if probability of post-operative infection is equal or higher than 75%; and a third level of alert may be generated if probability of post-operative infection alert is equal or higher than 90%.

Figure 5:
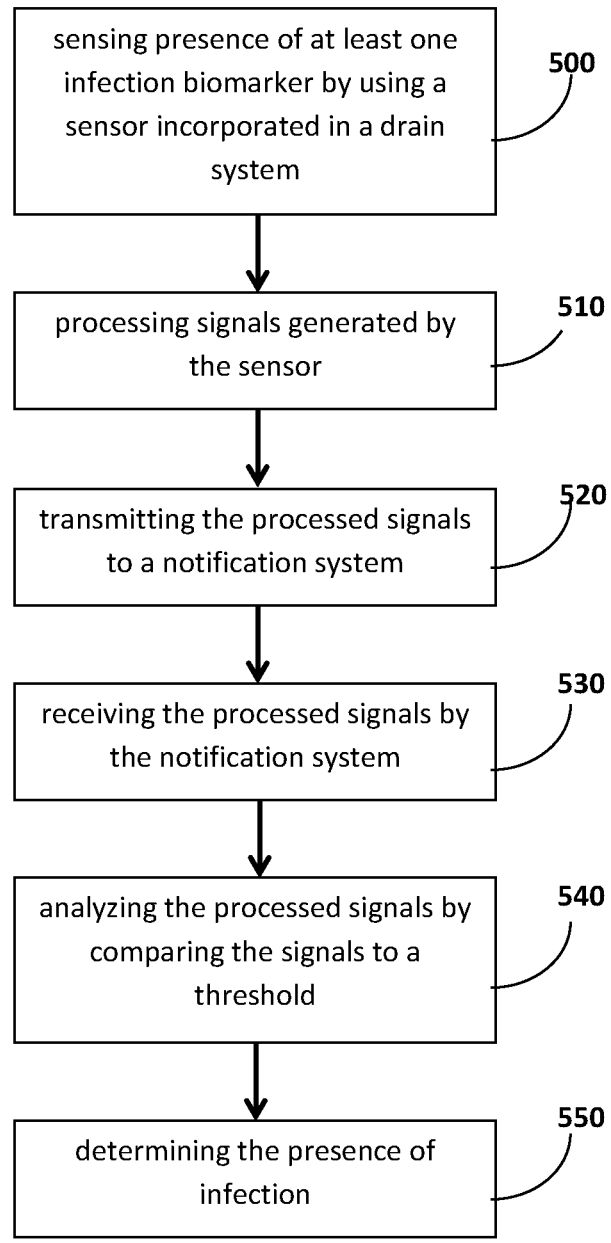
FIG. 5 is a flow chart depicting a method for determining early signs of post-surgery infection in a patient, in accordance with an embodiment of the invention.

Reference is now made to FIG. 5, which is a flow chart depicting a method for determining early signs of post-surgery infection in a patient, in accordance with an embodiment of the invention. According to some embodiments, a method for determining early signs of an infection in the surgical site may comprise the step of sensing presence of at least one infection biomarker by using a sensor incorporated in a drain system (500). The drain system may either be a closed loop drain system that comprises a container into which the exudates are drained, or an open loop drain system, in which the fluids are drained onto a dressing of some kind. The method may further comprise the steps of processing signals generated by the sensor (510), transmitting the processed signals to a notification system (520), and receiving the processed signals by the notification system (530). In some embodiments, transmission of the processed signals may be done wirelessly. In some embodiments, the notification system may be similar to notification system 109 (FIG. 4). In some embodiments, the system may further comprise the step of analyzing the processed signals by comparing the signals to a threshold (540). The threshold may either be a predetermined threshold or an adjustable threshold that may be constantly changed based on the trend of sensed parameters related to the infection biomarkers. According to some embodiments, the method may further comprise the step of determining the presence of infection (550). In some embodiments, the method may further comprise a step of determining the stage of infection and not only determining presence of an infection, e.g., whether the stage of the infection is mild, progressive or severe, though other stages may be defined by the user or operator of the system, e.g., system 200.

In some embodiments, the step of sensing presence of infection biomarkers is carried out continuously. In other embodiments, the step of sensing presence of infection biomarkers is carried out periodically. In some embodiments, periodical sensing may be adjusted per type of biomarker. For example, if the biomarker is pH, then sensing may be done in periods of less than 1 minute, and if the biomarker is bacteria specie, the sensing may be done every 10 minutes or less.

Figure 6:
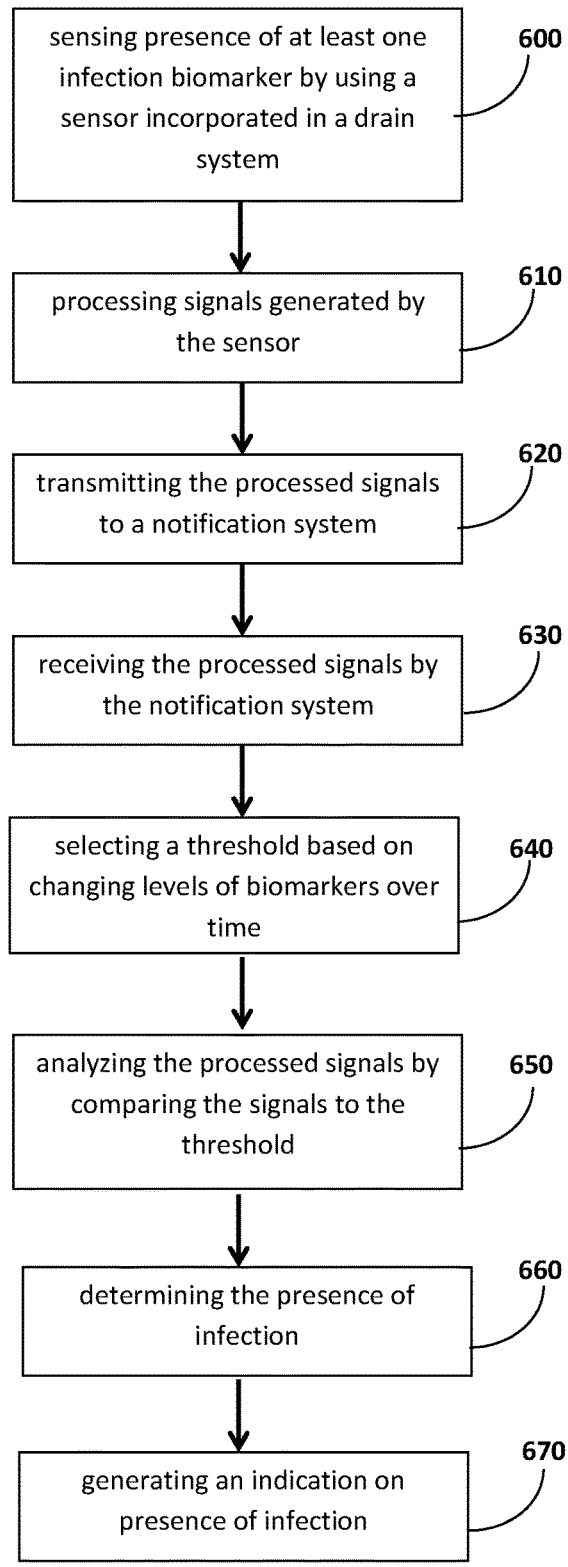
FIG. 6 is a flow chart depicting a method for determining early signs of post-surgery infection in a patient, in accordance with another embodiment of the invention.

Reference is now made to FIG. 6, which is a flow chart depicting a method for determining early signs of post-surgery infection in a patient, in accordance with another embodiment of the invention. According to some embodiments, a method for determining presence of an infection at a surgical site, following surgery of a patient, may comprise the following steps: sensing presence of at least one infection biomarker by using a sensor incorporated in a drain system (600), processing signals generated by the sensor (610), transmitting the processed signals to a notification system (620), and receiving the processed signals by the notification system (630). According to some embodiments, the method may further comprise the steps of selecting a threshold based on changing levels of biomarkers along time (640). The method may further comprise the step of analyzing the processed signals by comparing the signals to the threshold (650). In some embodiments, the threshold may be a predetermined threshold or may be an adjustable threshold that may be changed by the notification system according to the increase or decrease of the trend of the sensed parameters related to an infection biomarker or to a plurality of infection biomarkers, over time.

According to some embodiments, the method may further comprise the steps of determining the presence of infection (660), and generating an indication on presence of infection (670). In some embodiments, the method may comprise the step of generating an indication of the stage of infection, e.g., mild, progressive or severe, though other stages may be chosen, thus defining the corresponding level of the threshold.

In some embodiments, the step of sensing presence of infection biomarkers is carried out continuously. In other embodiments, the step of sensing presence of infection biomarkers is carried out periodically. In some embodiments, periodical sensing may be adjusted per type of biomarker. For example, if the biomarker is pH, then sensing may be done in periods of less than 1 minute, and if the biomarker is bacteria specie, the sensing may be done every 10 minutes or less.

Figure 7:
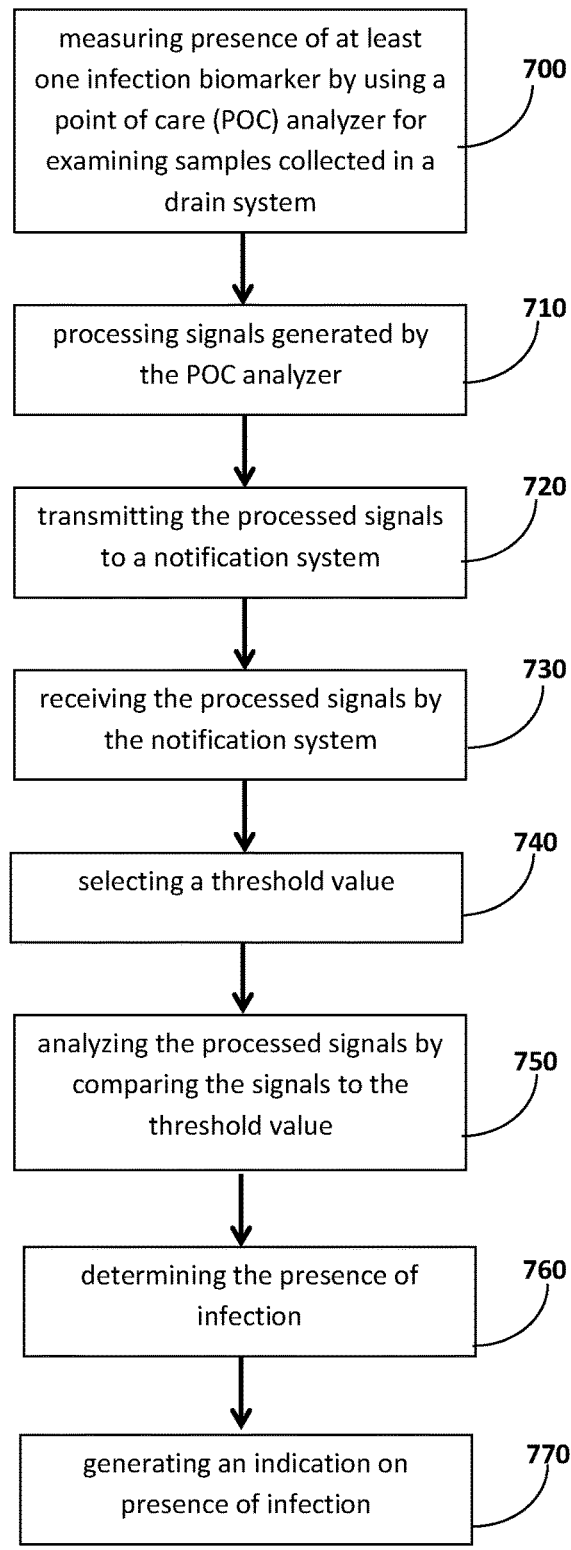
FIG. 7 is a flow chart depicting a method for determining early signs of post-surgery infection in a patient, in accordance with yet another embodiment of the invention.

Reference is now made to FIG. 7, which is a flow chart depicting a method for determining early signs of post-surgery infection in a patient, in accordance with yet another embodiment of the invention. According to some embodiments, when infection biomarkers cannot be sensed continuously along the tube, a method for determining early signs of post-surgery infection in a patient may comprise the steps of: measuring presence of at least one infection biomarker by using a point of care (POC) analyzer for examining samples collected in a drain system (700), processing signals generated by the POC analyzer (710), transmitting the processed signals to a notification system (720), and receiving the processed signals by the notification system (730). According to some embodiments, the method may further comprise the steps of selecting a threshold value (740) and analyzing the processed signals by comparing the signals to the threshold value (750). In some embodiments, the threshold may be a predetermined threshold or may be an adjustable threshold that may be changed by the notification system according to the increase or decrease of the trend of the sensed parameters related to an infection biomarker or to a plurality of infection biomarkers, over time.

According to some embodiments, the method may further comprise the step of determining the presence of infection (760). In some embodiments, the method may further comprise the step of generating an indication on presence of infection (770). In some embodiments, the method may comprise the step of generating an indication of the stage of infection, e.g., mild, progressive or severe, though other stages may be chosen, thus defining the corresponding level of the threshold.

In some embodiments, the POC analyzer may be incorporated in the drain system, while in other embodiments the POC analyzer may be located externally to the drain system while samples that are collected in a semi-continuously manner by the drain system may enter the POC analyzer, e.g., the POC analyzer may be fed with the samples collected by the drain system either manually, semi-automatically or fully-automatically.

It will be appreciated that the present invention is not limited to what has been particularly shown and described hereinabove. Rather the scope of the present invention is defined only by the claims which follow.

The invention claimed is:

1. A system for detecting early signs of post-surgery infection in a patient, said system comprising:

a drain system comprising a tube configured to drain fluids from a surgery site;

at least one sensor unit configured for sensing a presence of at least one infection biomarker, the at least one sensor unit located within the tube;

a processor configured for processing a signal generated by said at least one sensor unit;

a transmitter configured for transmitting the signal;

a notification system configured for receiving the signal, analyzing the signal by comparing the signal to a threshold, determining presence of an infection, and generating an indication on the presence of the infection, and wherein said at least one infection biomarker includes pH, a first indication is generated by the notification system if pH is equal to or below 7.1, and a second indication is generated by the notification system if the pH is equal to or below 6.8.

2. The system according to claim 1, wherein said at least one sensor unit comprises a memory unit.

3. The system according to claim 1, wherein said at least one sensor unit comprises a heating resistor for controlling a temperature within said at least one sensor unit.

4. The system according to claim 1, wherein said at least one sensor unit comprises an illumination source and a photodetector.

5. The system according to claim 4, wherein said at least one sensor unit further comprises a sol-gel material located between the illumination source and the photodetector.

6. The system according to claim 1, wherein said at least one sensor unit comprises at least a first and second sensor unit.

7. The system according to claim 1, further comprising a suction element for drawing the fluids from the surgery site through the tube.

8. The system according to claim 1, wherein said at least one infection biomarker is a direct infection biomarker.

9. The system according to claim 1, wherein the system further comprises another sensor unit configured for sensing at least a second infection biomarker selected from *Escherichia coli, Pseudomonas* spp., *Pseudomonas aeruginosa, Pseudomonas putida, Staphylococcus* spp., *Staphylococcus aureus, Staphylococcus epidermidis, Streptococcus* spp., *Enterococcus* spp., *Klebsiella* spp., *Proteus* spp., *Serratia* spp., *Morganella* spp. and other Enterobacteriaceae, or a combination thereof.

10. The system according to claim 9, wherein the notification system comprises an analyzer for analyzing signals detected by the at least one sensor unit and the another sensor unit and determining presence of the infection.

11. The system according to claim 1, wherein the notification system comprises an analyzer for analyzing a processed signal and determining presence of the infection.

12. The system according to claim 11, wherein the analyzer further determines a stage of the infection.

13. The system according to claim 1, wherein the indication is displayed on a display unit.

14. The system according to claim 1, wherein said at least one sensor unit senses the presence of said at least one infection biomarker continuously.

15. The system according to claim 1, wherein said at least one sensor unit senses the presence of said at least one infection biomarker periodically.

* * * * *

UNITED STATES PATENT AND TRADEMARK OFFICE
CERTIFICATE OF CORRECTION

PATENT NO. : 11,058,332 B2
APPLICATION NO. : 15/512251
DATED : July 13, 2021
INVENTOR(S) : Bayon Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 589 days.

Signed and Sealed this
Twenty-fourth Day of January, 2023

Katherine Kelly Vidal
*Director of the United States Patent and Trademark Office*